(12) United States Patent
Ambati et al.

(10) Patent No.: US 9,534,222 B2
(45) Date of Patent: Jan. 3, 2017

(54) MORPHOLINOS, MORPHOLINO UPREGULATING, AND ASSOCIATED METHODS

(71) Applicants: Balamurali K. Ambati, Sandy, UT (US); Hironori Uehara, Salt Lake City, UT (US)

(72) Inventors: Balamurali K. Ambati, Sandy, UT (US); Hironori Uehara, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 63 days.

(21) Appl. No.: 14/358,572

(22) PCT Filed: Nov. 15, 2012

(86) PCT No.: PCT/US2012/065320
§ 371 (c)(1),
(2) Date: May 15, 2014

(87) PCT Pub. No.: WO2013/074814
PCT Pub. Date: May 23, 2013

(65) Prior Publication Data
US 2016/0040169 A1 Feb. 11, 2016

Related U.S. Application Data

(60) Provisional application No. 61/559,833, filed on Nov. 15, 2011.

(51) Int. Cl.
*C12N 15/11* (2006.01)
*C12N 15/113* (2010.01)

(52) U.S. Cl.
CPC .......... *C12N 15/1138* (2013.01); *C12N 15/111* (2013.01); *C12N 2310/11* (2013.01); *C12N 2310/3233* (2013.01); *C12N 2320/33* (2013.01)

(58) Field of Classification Search
CPC .............. C12N 15/113; C12N 2310/30; C12N 2310/3233
See application file for complete search history.

(56) References Cited

U.S. PATENT DOCUMENTS

| | | | |
|---|---|---|---|
| 2003/0032160 A1 | 2/2003 | Kendall et al. | |
| 2003/0032609 A1 | 2/2003 | Lee et al. | |
| 2003/0229913 A1 | 12/2003 | Habeck et al. | |
| 2005/0287548 A1* | 12/2005 | Bao | B82Y 5/00 435/6.11 |
| 2006/0287268 A1* | 12/2006 | Iversen | C07F 9/65583 514/44 A |
| 2008/0269152 A1 | 10/2008 | Verdine et al. | |
| 2008/0318857 A1 | 12/2008 | Ambati et al. | |
| 2009/0186376 A1* | 7/2009 | Ambati | C07K 14/71 435/29 |
| 2010/0136001 A1* | 6/2010 | Sukhatme | A61K 31/711 514/1.1 |
| 2012/0029053 A1* | 2/2012 | Natt | C12N 15/1138 514/44 A |

FOREIGN PATENT DOCUMENTS

WO    WO 2013/074814 A2    5/2013

OTHER PUBLICATIONS

James Summerton (Current in Topics in Medicinal Chemistry, 2007, 7, 651-660).*
Wages et al. Biotechniques 1997 23:1116-21.*
Abdel-Rahman MH, Yang Y, Salem MM, Meadows S, Massengill JB, et. al. (2010) Investigation of the potential utility of a linomide analogue of treatment of choroidal neovascularization. Exp Eye Res Dec 91(6): 837-843.
Aiello LP, Pierce EA, Foley ED, Takagi H, Chen H, et. al. (1995) Suppression of retinal neovascularization in vivo by inhibition of vascular endothelial growth factor (VEGF) using soluble VEGF-receptor chimeric proteins. Proc Natl Acad Sci U S A 92: 10457-10461.
Albuquerque, R.J., Hayashi, T., Cho, W.G., Kleinman, M.E., Dridi, S., Takeda, A., Baffi, J.Z., Yamada, K., Kaneko, H., Green, M.G., et al. (2009). Alternatively spliced vascular endothelial growth factor receptor-2 is an essential endogenous inhibitor of lymphatic vessel growth. Nat Med 15, 1023-1030.
Alter J, Lou F, Rabinowitz A, Yin H, Rosenfeld J, et.al. (2006) Systemic delivery of morpholino oligonucleotide restores dystrophin expression bodywide and improves dystrophic pathology. Nature Medicine Feb. 12(2): 175-7.
Ambati BK, Nozaki M, Singh N, Takeda A, Jani PD, et. al. (2006) Corneal avascularity is due to soluble VEGF receptor-1. Nature Oct. 26; 443: 993-997.
Bertin S, Mohsen-Kanson T, Baqué P, Gavelli A, Momier D, et.al. (2010) Tumor microenvironment modifications induced by soluble VEGF receptor expression in a rat liver metastasis model. Cancer Lett Dec. 8;298(2):264-72.
Bhargava, P., and Robinson, M.O. (2011). Development of second-generation VEGFR tyrosine kinase inhibitors: current status. Curr Oncol Rep 13, 103-111.
Brown DM, Kaiser PK, Michels M, Soubrane G, Heier JS, et.al. (2006) Ranibizumab versus verteporfin for neovascular age-related macular degeneration. N EnglJ Med 355: 1432-1444.
Cao Y, Cao R, Hedlund EM. (2008) R Regulation of tumor angiogenesis and metastasis by FGF and PDGF signaling pathways. J Mol Med Jul.; 86(7): 785-89.

(Continued)

*Primary Examiner* — Brian Whiteman
(74) *Attorney, Agent, or Firm* — Thorpe North & Western, LLP

(57) ABSTRACT

Various methods and compositions relating to vascular endothelial growth factor receptor 2 (VEGFR2) are provided. In one aspect, a method of increasing expression of the soluble form of VEGFR2 (sVEGFR2) in a subject can include binding an antisense morphoiino to an exon13-intron13 splicing site of VEGFR2 mRNA such that the VEGFR2 niRNA is spliced into a sVEGFR2 isoform.

6 Claims, 17 Drawing Sheets

(56) References Cited

OTHER PUBLICATIONS

Carmeliet et al, Nature, 2000, 407, pp. 249-257.
Carmeliet et al, Nature, 2011, 473, pp. 298-307.
Ebos, J.M. et al. A naturally occurring soluble form of vascular endothelial growth factor receptor 2 detected in mouse and human plasma. *Mol Cancer Res* 2, 315-326 (2004).
Elkin M, Orgel A, and Kleinman HK (2004) An angiogenic switch in breast cancer involves estrogen and soluble vascular endothelial growth factor receptor 1. J Natl Cancer Inst Jun. 2;96(11):875-8.
Ellis, L.M., and Hicklin, D.J. (2008). VEGF-targeted therapy: mechanisms of anti-tumour activity. Nat Rev Cancer 8, 579-591.
Fischer, C., Mazzone, M., Jonckx, B., and Carmeliet, P. (2008). FLT1 and its ligands VEGFB and P1GF: drug targets for anti-angiogenic therapy? Nat Rev Cancer 8, 942-956.
Folkman J (1972) Anti-angiogenesis: new concept for therapy of solid tumors. Ann Surg Mar.; 175(3): 409-416.
Gasparini, G (2000) Prognostic Value of Vascular Endothelial Growth Factor in Breast Cancer. Oncologist 5(suppl 1):37-44.
Giovannini M, Aldrighetti D, Zucchinelli P, Belli C, and Villa E (2010) Antiangiogenic strategies in breast cancer management. Crit Rev Oncol Hematol Oct.;76(1):13-35.
Goldman, C.K., Kendall, R.L., Cabrera, G., Soroceanu, L., Heike, Y., Gillespie, G.Y., Siegal, G.P., Mao, X., Bett, A.J., Huckle, W.R., et al. (1998). Paracrine expression of a native soluble vascular endothelial growth factor receptor inhibits tumor growth, metastasis, and mortality rate. Proc Natl Acad Sci U S A 95, 8795-8800.
Hasumi Y, Mizukami H, Urabe M, Kohno T, Takeuchi K, et al. (2002) Soluble FLT-1 expression suppresses carcinomatous ascites in nude mice bearing ovarian cancer. Cancer Res Apr. 1;62(7):2019-23.
Hou X, Kumar A, Lee C, Wang B, Arjunan P, et. al. (2010) PDGF-CC blockade inhibits pathological angiogenesis by acting on multiple cellular and molecular targets. Proc Natl Acad Sci U S A Jul. 6 107(27): 12216-12221.
Kendall, R.L., and Thomas, K.A. (1993) Inhibition of vascular endothelial cell growth factor activity by an endogenously encoded soluble receptor. Proc Natl Acad Sci U S A 90, 10705-10709.
Kinali M, Arechavala-Gomeza V, Feng L, Cirak S, Hunt D et al (2009) Local restoration of dystropin expression with the morpholino oligomer AVI-4658 in Duchenne muscular dystrophy: a single blind, placebo-controlled, dose escalation, proof-of-concept study. Lancet Neurol Oct.; 8(10): 918-928.
Kishuku M, Nishioka Y, Abe S, Kishi J, Ogino H, et.al. (2009) Expression of soluble vascular endothelial growth factor receptor-1 in human monocyte-derived mature dendritic cells contributes to their antiangiogenic property. J Immunol Dec. 15:183(12): 8176-85.
Krzystolik MG, Afshari MA, Adamis AP, Gaudreault J, Gragoudas ES (2002) Prevention of experimental choroidal neovascularization with intravitreal anti-vascular endothelial growth factor antibody fragment. Arch Ophthalmol Mar.;120(3):338-46.
Lai CM, Shen WY, Brankov M, Lai YK, Barnett NL, et. al. (2005) Long-Term Evaluation of AAV-Mediated sFlt-1 Gene Therapy for Ocular Neovascularization in Mice and Monkeys. Mol Ther 12(4): 659-668.
Lukason M, DuFresne E, Rubin H, Pechan P, Li Q, et. al. (2011) Inhibition of choroidal neovascularization in a nonhuman primate model by intravitreal administration of an AAV2 vector expression a novel anti-VEGF molecule. Mol Ther Feb.; 19(2): 260-5.
Meissner, M., Reichenbach, G., Stein, M., Hrgovic, I., Kaufmann, R., and Gille, J. (2009). Down-regulation of vascular endothelial growth factor receptor 2 is a major molecular determinant of proteasome inhibitor-mediated antiangiogenic action in endothelial cells. Cancer Res 69, 1976-1984.
Miles DW, Chan A, Dirix LY, Cortés J, Pivot X, et. al. (2010) Phase III study of bevacizumab plus docetaxel compared with placebo plus docetaxel for the first-line treatment of human epidermal growth factor receptor 2-negative metastatic breast cancer. J Clin Oncol Jul. 10;28(20):3239-47.
Morcos et al, "Vivo-Morpholinos: A Non-Peptide Transporter Delivers Morpholinos into a Wide Array of Mouse Tissue", BioTechniques, 2008, pp. 613-623, vol. 45, No. 6.
Nieto Y, Woods J, Nawaz F, Baron A, Jones RB, et. al. (2007) Prognostic analysis of tumour angiogenesis, determined by microvessel density and expression of vascular endothelial growth factor, in high-risk primary breast cancer patients treated with highdose chemotherapy. Br J Cancer 97, 391-397.
Nissen LJ, Cao R, Hedlund EM, Wang Z, Zhao X, et.al. (2007) Angiogenic factors FGF2 and PDGFBB synergistically promote murine tumor neovascularization and metastasis. J Clin Invest Oct. 117(10): 2766-77.
Ogawa, T., Takayama, K., Takakura, N., Kitano, S., and Ueno, H. (2002). Anti-tumor angiogenesis therapy using soluble receptors enhanced inhibition of tumor growth when soluble fibroblast growth factor receptor-1 is used with soluble vascular endothelial growth factor receptor. Cancer Gene Ther 9, 633-640.
Ozaki H, Hayashi H, Vinores SA, Moromizato Y, Campochiaro PA and Oshima K (1997) Intraviteral sustained release of VEGF causes retinal neovascularizaiton in rabbits and breakdown of the blood retinal barrier in rabbits and primates. Exp Eye Res 64: 505-517.
Reiter, J.L., and Maihle, N.J. (1996). A 1.8 kb alternative transcript from the human epidermal growth factor receptor gene encodes a truncated form of the receptor. Nucleic Acids Res 24, 4050-4056.
Ruffini F, Failla CM, Orecchia A, Bani MR, Dorio AS, et.al. (2011) Expression of the soluble vascular endothelial growth factor receptor-1 in cutaneous melanoma: role in tumour progression. Br J Dermatol May;164(5):1061-70.
Sela, S., Itin, A., Natanson-Yaron, S., Greenfield, C., Goldman-Wohl, D., Yagel, S., and Keshet, E. (2008). A novel human-specific soluble vascular endothelial growth factor receptor 1: cell-type-specific splicing and implications to vascular endothelial growth factor homeostasis and preeclampsia. Circ Res 102, 1566-1574.
Shibuya, M. (2006). Vascular endothelial growth factor receptor-1 (VEGFR-1/Flt-1): a dual regulator for angiogenesis. Angiogenesis 9, 225-230; discussion 231.
Shibuya, M. Differential roles of vascular endothelial growth factor receptor-1 and receptor-2 in angiogenesis. *J Biochem Mol Biol* 39, 469-478 (2006).
Shibuya, M. Vascular endothelial growth factor-dependent and -independent regulation of angiogenesis. BMB Rep 41, 278-286 (2008).
Summerton, "Morpholino, siRNA, and S-DNA Compared: Impact of Structure and Mechanism of Action on Off-Target Effects and Sequence Specificity", Current Topics in Medicinal Chemistry, 2007, pp. 651-660, vol. 7, Bentham Science Publishers Ltd.
Summerton, J. Morpholino antisense oligomers: the case for an RNase H-independent structural type. Biochim Biophys Acta 1489, 141-158 (1999).
Takahashi, T. & Shibuya, M. The 230 kDa mature form of KDR/Flk-1 (VEGF receptor-2) activates the PLC-gamma pathway and partially induces mitotic signals in NIH3T3 fibroblasts. *Oncogene* 14, 2079-2089 (1997).
Tolentino MJ, McLeod DS, Taomoto M, Otsuji T, Adamis AP and Lutty GA (2002) Pathologic features of vascular endothelial growth factor induced retinopathy in the nonhuman primate. Am J Ophthalmol 133: 373-385.
Vivanco, I., and Mellinghoff, I.K. (2010). Epidermal growth factor receptor inhibitors in oncology. Curr Opin Oncol 22, 573-578.
Wong CG, Rich KA, Liaw LH, Hsu HT, Berns MW. (2001) Intravitreal VEGF and bFGF produce florid retinal neovascularization and hemorrhage in the rabbit. Curr Eye Res Feb. 22(2): 140-147.

* cited by examiner

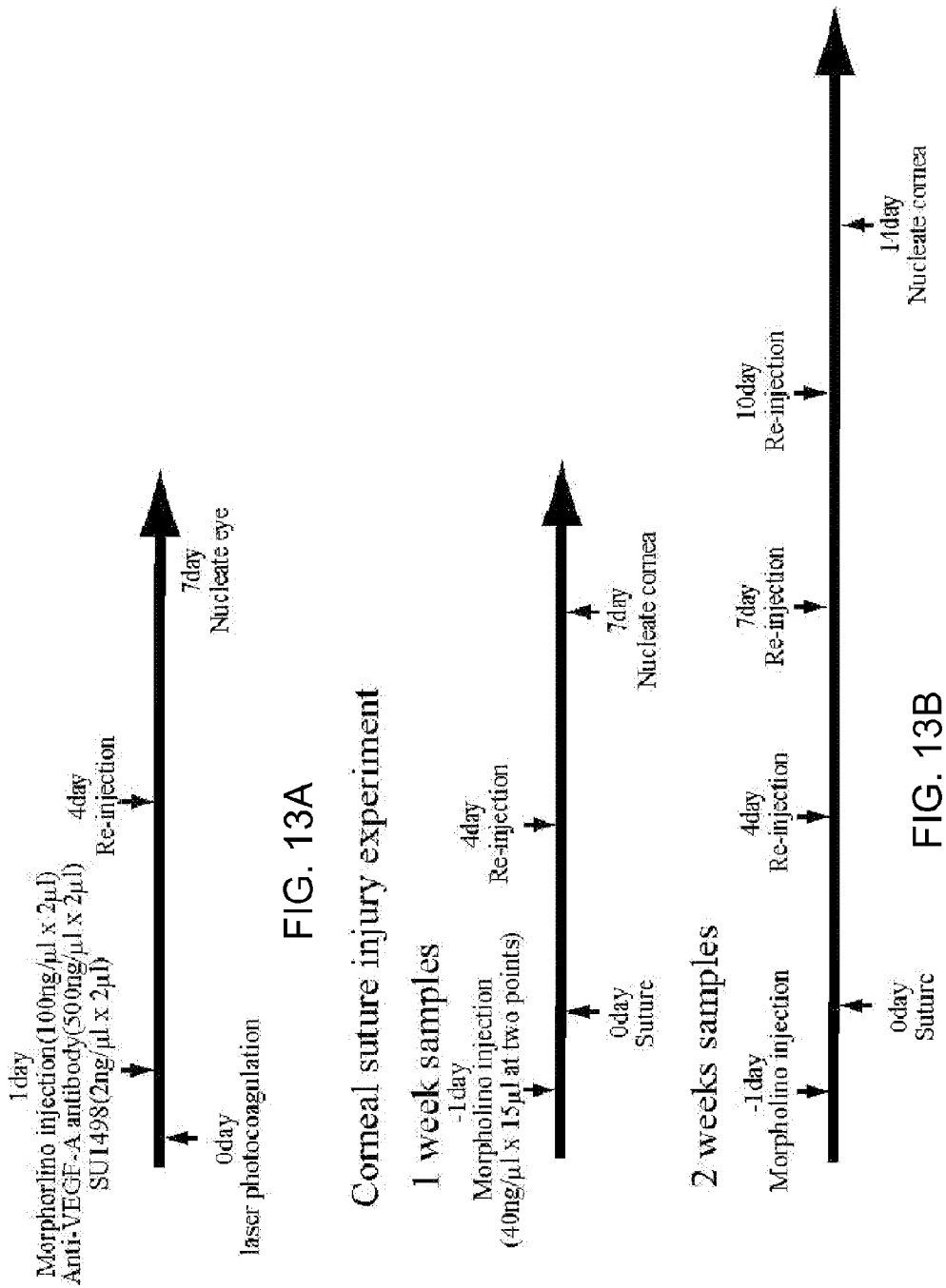

SEQUENCE LISTING

```
<160> NUMBER OF SEQ ID NOS: 43

<210> SEQ ID NO 1
<211> LENGTH: 25
<212> TYPE: DNA
```

<213> ORGANISM: Human

<400> SEQUENCE: 1
gatccagaat tgtctcccta cctag                                          25

<210> SEQ ID NO 2
<211> LENGTH: 25
<212> TYPE: DNA
<213> ORGANISM: Human

<400> SEQUENCE: 2
ccacacgctc tagacacaca aaaag                                          25

<210> SEQ ID NO 3
<211> LENGTH: 25
<212> TYPE: DNA
<213> ORGANISM: Mouse

<400> SEQUENCE: 3
cacccaggga tgcctccata cctag                                          25

<210> SEQ ID NO 4
<211> LENGTH: 20
<212> TYPE: DNA
<213> ORGANISM: Human

<400> SEQUENCE: 4
ttcttggctg tgcaaaagtg                                                20

<210> SEQ ID NO 5
<211> LENGTH: 20
<212> TYPE: DNA
<213> ORGANISM: Human

<400> SEQUENCE: 5
tcttcagttc ccctccattg                                                20

<210> SEQ ID NO 6
<211> LENGTH: 20
<212> TYPE: DNA
<213> ORGANISM: Human

<400> SEQUENCE: 6
gagagttgcc cacacctgtt                                                20

<210> SEQ ID NO 7
<211> LENGTH: 20
<212> TYPE: DNA
<213> ORGANISM: Human

<400> SEQUENCE: 7
caactgcctc tgcacaatga                                                20

<210> SEQ ID NO 8
<211> LENGTH: 20
<212> TYPE: DNA
<213> ORGANISM: Human

<400> SEQUENCE: 8
cctaccagta cggcaccact                                                20

<210> SEQ ID NO 9
<211> LENGTH: 20

```
<212> TYPE: DNA
<213> ORGANISM: Human

<400> SEQUENCE: 9
cagcctcaag atcatcagca                                               20

<210> SEQ ID NO 10
<211> LENGTH: 20
<212> TYPE: DNA
<213> ORGANISM: Human

<400> SEQUENCE: 10
tgtggtcatg agtccttcca                                               20

<210> SEQ ID NO 11
<211> LENGTH: 20
<212> TYPE: DNA
<213> ORGANISM: Mouse

<400> SEQUENCE: 11
accaaggcga ctatgtttgc                                               20

<210> SEQ ID NO 12
<211> LENGTH: 20
<212> TYPE: DNA
<213> ORGANISM: Mouse

<400> SEQUENCE: 12
caattctgtc acccagggat                                               20

<210> SEQ ID NO 13
<211> LENGTH: 20
<212> TYPE: DNA
<213> ORGANISM: Mouse

<400> SEQUENCE: 13
accattgaag tgacttgccc                                               20

<210> SEQ ID NO 14
<211> LENGTH: 20
<212> TYPE: DNA
<213> ORGANISM: Mouse

<400> SEQUENCE: 14
ccggttccca tctctcagta                                               20

<210> SEQ ID NO 15
<211> LENGTH: 24
<212> TYPE: DNA
<213> ORGANISM: Mouse

<400> SEQUENCE: 15
aactttggca ttgtggaagg gctc                                          24

<210> SEQ ID NO 16
<211> LENGTH: 24
<212> TYPE: DNA
<213> ORGANISM: Mouse

<400> SEQUENCE: 16
accagtggat gcaggatga tgtt                                           24

<210> SEQ ID NO 17
```

```
<211> LENGTH: 38
<212> TYPE: DNA
<213> ORGANISM: Artificial Sequence
<220> FEATURE:
<223> OTHER INFORMATION: completely synthesized

<400> SEQUENCE: 17
ggccacgcgt cgactagtac ttttttttt tttttttv                                38

<210> SEQ ID NO 18
<211> LENGTH: 20
<212> TYPE: DNA
<213> ORGANISM: Artificial Sequence
<220> FEATURE:
<223> OTHER INFORMATION: completely sequenced

<400> SEQUENCE: 18
ggccacgcgt cgactagtac                                                   20

<210> SEQ ID NO 19
<211> LENGTH: 20
<212> TYPE: DNA
<213> ORGANISM: Artificial Sequence
<220> FEATURE:
<223> OTHER INFORMATION: completely sequenced

<400> SEQUENCE: 19
ccagcatcct tcaagtcaca                                                   20

<210> SEQ ID NO 20
<211> LENGTH: 25
<212> TYPE: DNA
<213> ORGANISM: human

<400> SEQUENCE: 20
acacgctcta gacacacaaa aagaa                                             25

<210> SEQ ID NO 21
<211> LENGTH: 25
<212> TYPE: DNA
<213> ORGANISM: human

<400> SEQUENCE: 21
gatccagaat tgtctcccta cctag                                             25

<210> SEQ ID NO 22
<211> LENGTH: 25
<212> TYPE: DNA
<213> ORGANISM: human

<400> SEQUENCE: 22
acactttaga tttattcttt cttca                                             25

<210> SEQ ID NO 23
<211> LENGTH: 25
<212> TYPE: DNA
<213> ORGANISM: human

<400> SEQUENCE: 23
ctagaatgaa tccttacctg caagt                                             25

<210> SEQ ID NO 24
<211> LENGTH: 26
<212> TYPE: DNA
<213> ORGANISM: human
```

-continued

<400> SEQUENCE: 24
atgatccaga attgtctccc taccta                                          26

<210> SEQ ID NO 25
<211> LENGTH: 26
<212> TYPE: DNA
<213> ORGANISM: human

<400> SEQUENCE: 25
tgatccagaa ttgtctccct acctag                                          26

<210> SEQ ID NO 26
<211> LENGTH: 26
<212> TYPE: DNA
<213> ORGANISM: human

<400> SEQUENCE: 26
atccagaatt gtctccctac ctagga                                          26

<210> SEQ ID NO 27
<211> LENGTH: 25
<212> TYPE: DNA
<213> ORGANISM: human

<400> SEQUENCE: 27
tccagaattg tctccctacc tagga                                           25

<210> SEQ ID NO 28
<211> LENGTH: 25
<212> TYPE: DNA
<213> ORGANISM: human

<400> SEQUENCE: 28
ccagaattgt ctccctacct aggac                                           25

<210> SEQ ID NO 29
<211> LENGTH: 25
<212> TYPE: DNA
<213> ORGANISM: human

<400> SEQUENCE: 29
cagaattgtc tccctaccta ggact                                           25

<210> SEQ ID NO 30
<211> LENGTH: 25
<212> TYPE: DNA
<213> ORGANISM: human

<400> SEQUENCE: 30
agaattgtct ccctacctag gactg                                           25

<210> SEQ ID NO 31
<211> LENGTH: 25
<212> TYPE: DNA
<213> ORGANISM: human

<400> SEQUENCE: 31
gaattgtctc cctacctagg actgt                                           25

<210> SEQ ID NO 32
<211> LENGTH: 25
<212> TYPE: DNA

```
<213> ORGANISM: human

<400> SEQUENCE: 32
aattgtctcc ctacctagga ctgtg                                              25

<210> SEQ ID NO 33
<211> LENGTH: 25
<212> TYPE: DNA
<213> ORGANISM: human

<400> SEQUENCE: 33
attgtctccc tacctaggac tgtga                                              25

<210> SEQ ID NO 34
<211> LENGTH: 25
<212> TYPE: DNA
<213> ORGANISM: human

<400> SEQUENCE: 34
ttgtctccct acctaggact gtgag                                              25

<210> SEQ ID NO 35
<211> LENGTH: 25
<212> TYPE: DNA
<213> ORGANISM: human

<400> SEQUENCE: 35
tgtctcccta cctaggactg tgagc                                              25

<210> SEQ ID NO 36
<211> LENGTH: 25
<212> TYPE: DNA
<213> ORGANISM: human

<400> SEQUENCE: 36
gtctccctac ctaggactgt gagct                                              25

<210> SEQ ID NO 37
<211> LENGTH: 25
<212> TYPE: DNA
<213> ORGANISM: human

<400> SEQUENCE: 37
tctccctacc taggactgtg agctg                                              25

<210> SEQ ID NO 38
<211> LENGTH: 25
<212> TYPE: DNA
<213> ORGANISM: human

<400> SEQUENCE: 38
ctccctacct aggactgtga gctgc                                              25

<210> SEQ ID NO 39
<211> LENGTH: 25
<212> TYPE: DNA
<213> ORGANISM: human

<400> SEQUENCE: 39
tccctaccta ggactgtgag ctgcc                                              25

<210> SEQ ID NO 40
<211> LENGTH: 25
```

```
<212> TYPE: DNA
<213> ORGANISM: human

<400> SEQUENCE: 40
ccctacctag gactgtgagc tgcct                                              25

<210> SEQ ID NO 41
<211> LENGTH: 25
<212> TYPE: DNA
<213> ORGANISM: human

<400> SEQUENCE: 41
cctacctagg actgtgagct gcctg                                              25

<210> SEQ ID NO 42
<211> LENGTH: 25
<212> TYPE: DNA
<213> ORGANISM: human

<400> SEQUENCE: 42
ctacctagga ctgtgagctg cctga                                              25

<210> SEQ ID NO 43
<211> LENGTH: 25
<212> TYPE: DNA
<213> ORGANISM: human

<400> SEQUENCE: 43
tacctaggac tgtgagctgc ctgac                                              25
```

MORPHOLINOS, MORPHOLINO UPREGULATING, AND ASSOCIATED METHODS

GOVERNMENT INTEREST

This invention was made with government support under grant number R01 EY017950 awarded by National Institutes of Health. The government has certain rights in the invention.

BACKGROUND OF THE INVENTION

Vascular endothelial growth factor (VEGF) is a signal protein produced by cells that stimulates lymphangiogenesis and angiogenesis. This system is partially responsible for the restoration of the oxygen supply to tissues when blood circulation is inadequate. VEGF's normal function is to create new blood vessels during embryonic development, new blood vessels after injury, in muscle following exercise, and new vessels (collateral circulation) to bypass blocked vessels. VEGF is a sub-family of growth factors, namely the platelet-derived growth factor family of cystine-knot growth factors. They are important signaling proteins involved in both lymphangiogenesis and angiogenesis.

When VEGF is overexpressed, it can contribute to various disease conditions. Solid cancers cannot grow beyond a limited size without an adequate blood supply, and thus cancers that can express VEGF are able to grow and metastasize. Overexpression of VEGF can also cause vascular disease in the retina of the eye and other parts of the body. Drugs such as bevacizumab have been used in an attempt to inhibit VEGF and control or slow those diseases.

Members of the VEGF family stimulate cellular responses by binding to tyrosine kinase receptors (the VEGFRs) on the cell surface, causing them to dimerize and become activated through transphosphorylation, although to different sites, times and extents. The VEGF receptors have an extracellular portion consisting of 7 immunoglobulin-like domains, a single transmembrane spanning region, and an intracellular portion containing a split tyrosine-kinase domain. VEGFR-2 appears to mediate almost all of the known cellular responses to VEGF. The function of VEGFR-1 is less well-defined, although it is thought to modulate VEGFR-signaling.

SUMMARY OF THE INVENTION

Various methods and compositions relating to vascular endothelial growth factor receptor 2 (VEGFR2) are provided. In one aspect, for example, a method of increasing expression of the soluble form of VEGFR2 (sVEGFR2) in a subject can include binding an antisense morpholino to an exon13-intron13 splicing site of VEGFR2 mRNA such that the VEGFR2 mRNA is spliced into a sVEGFR2 isoform. In one specific aspect, the morpholino can bind to the splicing site with a homology of greater than about 75%. In another specific aspect, the morpholino can bind to the splicing site with a homology of greater than about 95%. In yet another specific aspect, the morpholino can be at least about 75% homologous to SEQ ID 001. In a further specific aspect, the morpholino can be at least about 95% homologous to SEQ ID 001. In yet a further aspect, the morpholino can have a sequence of SEQ ID 001.

In another aspect, a method of inhibiting neovascularization in a subject is provided. Such a method can include binding an antisense morpholino to an exon13-intron13 splicing site of VEGFR2 mRNA such that the VEGFR2 mRNA is spliced into an sVEGFR2 isoform. In one specific aspect, the morpholino can bind to the splicing site with a homology of greater than about 75%. In another specific aspect, the morpholino can bind to the splicing site with a homology of greater than about 95%. In yet another specific aspect, the morpholino can be at least about 75% homologous to SEQ ID 001. In a further specific aspect, the morpholino can be at least about 95% homologous to SEQ ID 001. In yet a further aspect, the morpholino can have a sequence of SEQ ID 001.

In another aspect, a pharmaceutical composition for increasing expression of sVEGFR2 in a subject is provided. Such a composition can include a pharmaceutically effective carrier including a morpholino capable of binding to an exon13-intron13 splicing site of VEGFR2 mRNA to facilitate increased expression of sVEGFR2. In one specific aspect, the morpholino sequence can be at least about 75% homologous to the splicing site sequence. In another specific aspect, the morpholino sequence can be at least about 95% homologous to the splicing site sequence. In yet another specific aspect, the morpholino can include an oligomer selected from SEQ ID 001 to SEQ ID 043. In a further specific aspect, the morpholino can have a sequence of SEQ ID 001.

There has thus been outlined, rather broadly, various features of the invention so that the detailed description thereof that follows may be better understood, and so that the present contribution to the art may be better appreciated. Other features of the present invention will become clearer from the following detailed description of the invention, taken with the accompanying claims, or may be learned by the practice of the invention.

DETAILED DESCRIPTION OF THE INVENTION

Definitions

Figure 1A:
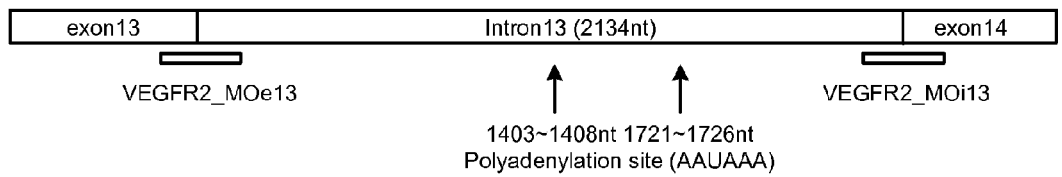
FIG. 1 provides data showing that VEGFR2_MOe13 decreases mbVEGFR2 and increases sVEGFR2 mRNA in accordance with one embodiment of the present invention.

In describing and claiming the present invention, the following terminology will be used in accordance with the definitions set forth below.

The singular forms "a," "an," and, "the" include plural referents unless the context clearly dictates otherwise. Thus, for example, reference to "a morpholino" includes reference to one or more of such morpholinos, and reference to "the oligomer" includes reference to one or more of such oligomers.

As used herein, the term "mRNA" can be used to describe sequences of mRNA and sequences of pre-mRNA, irrespective of the degree of splicing that has occurred in the sequence.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

The Invention

Alternative polyadenylation, considered part of alternative splicing, helps generate diverse mRNA and protein from a limited set of genes. Polyadenylation sites occur in the 3' untranslated region (3'UTR) of genes and result in different 3'UTRs which can affect mRNA stability and cellular location. Alternate polyadenylation sites exist in specific exons or introns of a given gene resulting in functional changes to proteins translated from that gene. One example, of such a gene is the vascular endothelial growth factor receptor 2 (VEGFR2, also referred as KDR/Flk1) gene, which participates at least in angiogenesis, vasculogenesis, and lymphangiogenesis. Many diseases (e.g., cancer, rheumatoid arthritis, macular degeneration, diabetic retinopathy) are due to uncontrolled neovascularization. Vascular endothelial growth factor A (VEGF-A) and VEGFR2 play central roles in physiological and pathological angiogenesis.

The VEGFR2 gene produces at least two functionally distinct protein products, membrane bound VEGFR2 (mbVEGFR2) and its isoform soluble VEGFR2 (sVEGFR2) by alternative polyadenylation. mbVEGFR2 has an extracellular domain including seven immunoglobulin domains, a transmembrane domain, and tyrosine kinase domains, and is the primary angiogenic receptor for VEGF-A. While mbVEGFR2 is comprised of 30 exons in humans and mice, sVEGFR2 is produced by utilization of polyadenylation signals within intron 13 in mice. Since sVEGFR2 does not have the tyrosine kinase domains of mbVEGFR2 and has much more affinity for VEGF-C than VEGF-A, sVEGFR2 may be an antagonist of mbVEGFR2 by binding to vascular endothelial growth factor A (VEGF-A) or vascular endothelial growth factor C (VEGF-C), an important driver of lymphangiogenesis. Thus, the membrane-bound isoform of VEGFR2 is prohemangiogenic, while the soluble isoform is antilymphangiogenic.

As has been described, the VEGFR2 gene produces both membrane-bound and soluble isoforms of VEGFR2. The latent polyadenylation site in intron 13 of KDR can be activated by blocking the upstream 5' splicing site with, for example, an antisense morpholino oligomer. Alternative polyadenylation of exon30 or intron13 of VEGFR2 can lead to the production of mbVEGFR2 or sVEGFR2, respectively. For example, in human umbilical vein endothelial cells (HUVECs), sVEGFR2 is usually not activated. Such activation can be accomplished by shift splicing VEGFR2 pre-mRNA from the membrane to the soluble isoform using a morpholino antisense oligomer. In addition, morpholino intravitreal injection suppresses laser choroidal neovascularization while increasing vitreous sVEGFR2. Furthermore, in a mouse corneal suturing model, injection of the morpholino into the subconjunctival space suppresses corneal angiogenesis and lymphangiogenesis, and suppresses graft rejection in mouse corneal transplantation. Such results indicate that exon recognition by splicing factors affects subsequent polyadenylation signal activation and that by modifying it, latent polyadenylation signals can be activated, inducing alternative isoforms of proteins. As such, the present disclosure elucidates alternative polyadenylation and indicates a new drug target through the modification of this mechanism. In some aspects, therefore, this morpholino can be used for, among other things, concurrent suppression of hemangiogenesis and lymphangiogenesis.

Figure 1B:
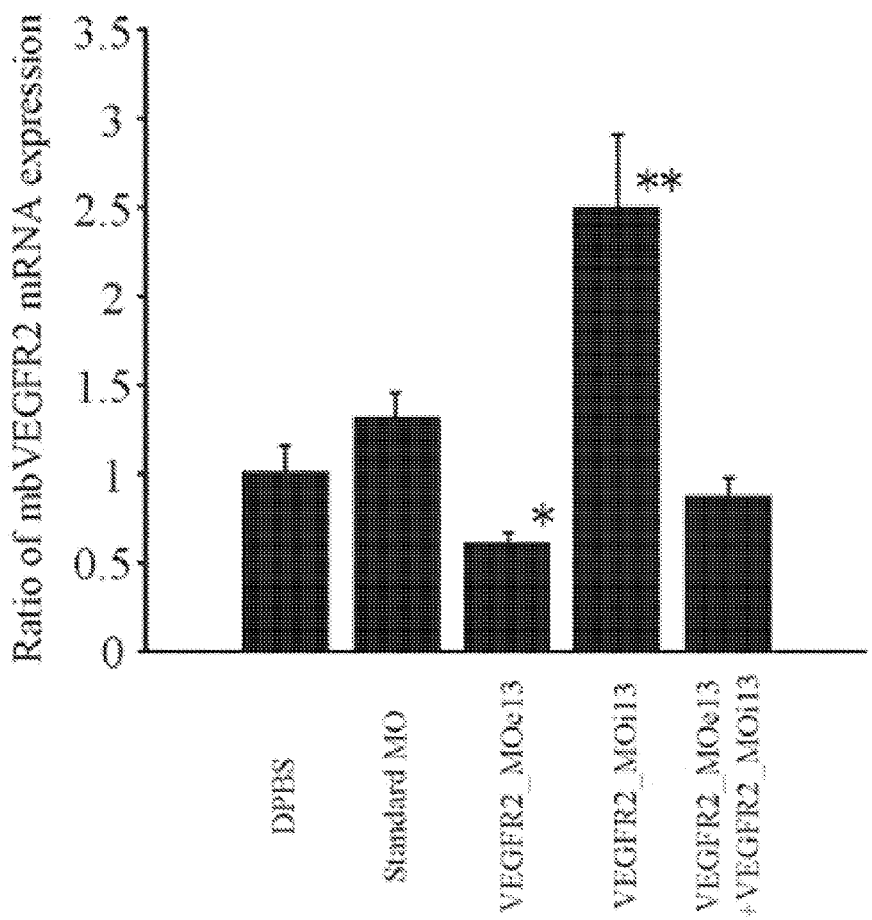
Figure 1C:
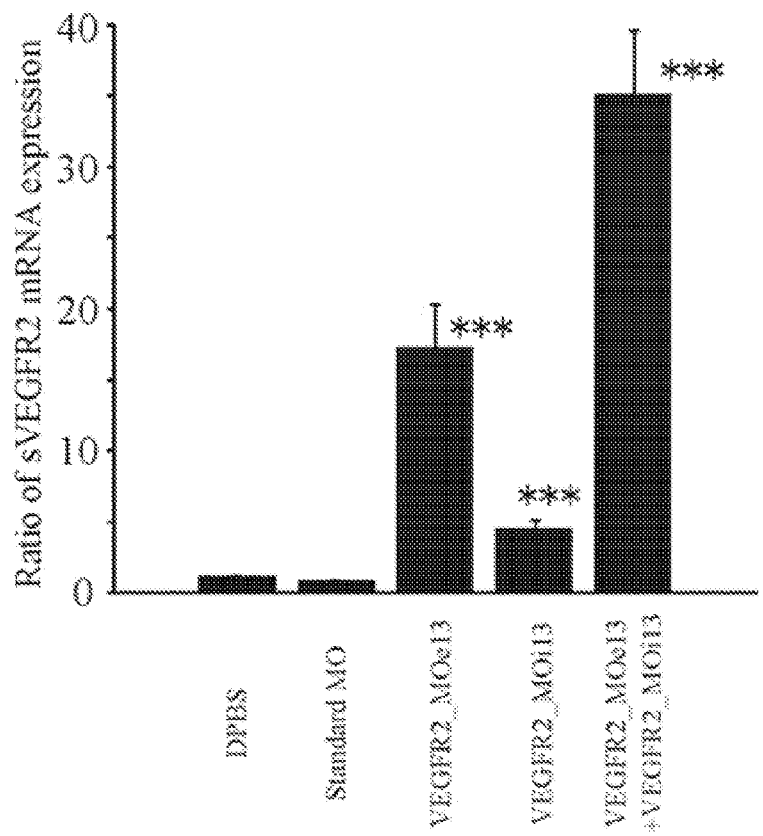

Although human sVEGFR2 mRNA structure is not well characterized, the expressed sequence tags database shows the sequence of the initial 365 nt of human intron13, which include a stop codon at 48-50 nt. In addition, two polyadenylation sites (AAUAAA) are found in intron13 (FIG. 1A). FIG. 1 shows that VEGFR2_MOe13 decreases mbVEGFR2 and increases sVEGFR2 mRNA, as is described more fully below. FIG. 1(a) illustrates a schematic design of anti-sense morpholino oligomers. FIG. 1(b, c) show the results of mbVEGFR2 and sVEGFR2 mRNA expression quantified by real-time PCR after morpholino transfection. All results are normalized by GAPDH expression and compared with DPBS transfected HUVECs as 1. p: risk factor by two-tail student's t-test. *:p<0.05, p<0.01, *p<0.001 compared with DPBS transfected HUVECs; n=6 for all groups: Error bar is ±s.e.m. It is thus concluded that human polyadenylation of sVEGFR2 mRNA occurs in intron13, and thus the present disclosure examines whether disruption of splicing between exon13-exon14 upregulates sVEGFR2.

In one aspect of the present disclosure, splicing can be modulated using anti-sense morpholino oligomers that bind mRNA or pre-mRNA with high specificity to inhibit translation and affect alternative splicing. Furthermore, since morpholino oligomers are RNase H-independent, RNA bound by morpholino oligomers is not degraded. Antisense morpholino oligomers can thus be designed corresponding to the junction of exon13-intron13 (VEGFR2_MOe13) and/or intron13-exon14 (VEGFR2_MOi13), respectively (FIG. 1A and the sequences in Table 1; it is noted that upper and lower case in morpholino oligomer sequences in Tables 1 and 2 correspond to exon and intron, respectively). A variety of potential antisense morpholino oligomers can be designed to bind to the junction of exon13-intron13 and/or intron13-exon14. Non-limiting examples of additional morpholinos are shown that correspond to VEGFR2_MOe13 are shown in Table 2. In one aspect, the latent polyadenylation site in intron13 of VEGFR2 can thus be activated by blocking the upstream 5' slicing site with an antisense morpholino oligomer. Intravitreal morpholino injections, for example, can suppress laser choroidal neovascularization while increasing sVEGFR2. Additionally, in the mouse cornea, subconjunctival injection of such morpholinos can inhibit corneal angiogenesis and lymphangiogenesis, as well as suppressing graft rejection after transplantation.

TABLE 1

Morpholino oligomer and primer sequences

| Oligomer or primer | Sequence |
|---|---|
| Morpholino oligomer | |
| VEGFR2_MOe13 (human) | 5'-gatccagaattgtctccctacCTAG-3' (SEQ ID 001) |
| VEGFR2_MOi13 (human) | 5'-CCACACGCTctagacacacaaaaag-3' (SEQ ID 002) |
| moVEGFR_MOe13 (mouse) | 5'-cacccagggatgcctccatacCTAG-3' (SEQ ID 003) |
| PCR primer for human | |
| sVEGFR2_F (exon13) | 5'-TTCTTGGCTGTGCAAAAGTG-3' (SEQ ID 004) |
| sVEGFR2_R (intron13) | 5'-TCTTCAGTTCCCCTCCATTG-3' (SEQ ID 005) |
| mbVEGFR2_F (exon15) | 5'-GAGAGTTGCCCACACCTGTT-3' (SEQ ID 006) |
| mbVEGFR2_R (exon17) | 5'-CAACTGCCTCTGCACAATGA-3' (SEQ ID 007) |
| VEGFR2exon10_F | 5'-CCTACCAGTACGGCACCACT-3' (SEQ ID 008) |
| GAPDH_F | 5'-CAGCCTCAAGATCATCAGCA-3' (SEQ ID 009) |
| GADPH_R | 5'-TGTGGTCATGAGTCCTTCCA-3' (SEQ ID 010) |
| PCR primer for mouse | |
| Mouse sVEGFR2_F | 5'-ACCAAGGCGACTATGTTTGC-3' (SEQ ID 011) |
| Mouse sVEGFR2_R | 5'-CAATTCTGTCACCCAGGGAT-3' (SEQ ID 012) |
| Mouse mbVEGFR2_F | 5'-ACCATTGAAGTGACTTGCCC-3' (SEQ ID 013) |
| Mouse mbVEGFR2_R | 5'-CCGGTTCCCATCTCTCAGTA-3' (SEQ ID 014) |

TABLE 1-continued

Morpholino oligomer and primer sequences

| Oligomer or primer | Sequence |
|---|---|
| Mouse GAPDH_F | 5'-AACTTTGGCATTGTGGAAGGGCTC-3'<br>(SEQ ID 015) |
| Mouse GAPDH_R | 5'-ACCAGTGGATGCAGGGATGATGTT-3'<br>(SEQ ID 016) |
| 3' RACE primer | |
| Cloning_R1 | 5'-GGCCACGCGTCGACTAGTACTTTTTTTTTTTTTTTTV-3'<br>(SEQ ID 017) |
| Cloning_R2 | 5'-GGCCACGCGTCGACTAGTAC-3'<br>(SEQ ID 018) |
| Cloning_F (1042-1061) | 5'-CCAGCATCCTTCAAGTCACA-3'<br>(SEQ ID 019) |

TABLE 2

Morpholino sequences

| | |
|---|---|
| SEQ ID 020 | ACACGCTCTAGACACACAAAAA-GAA |
| SEQ ID 021 | GATCCAGAATTGTCTCCCTACCTAG |
| SEQ ID 022 | ACAC-TTTAGATTTATTCTTTCTTCA |
| SEQ ID 023 | CTAGAATGAATCCTTACCTGCA-AGT |

Potential VEGFR2_MOe13 morpholinos

| | |
|---|---|
| SEQ ID 024 | atgatccagaattgtctccctacCTA |
| SEQ ID 025 | tgatccagaattgtctccctacCTAG |
| SEQ ID 001 | gatccagaattgtctccctacCTAGG |
| SEQ ID 026 | atccagaattgtctccctacCTAGGA |
| SEQ ID 027 | tccagaattgtctccctacCTAGGAC |
| SEQ ID 028 | ccagaattgtctccctacCTAGGAC |
| SEQ ID 029 | cagaattgtctccctacCTAGGACT |
| SEQ ID 030 | agaattgtctccctacCTAGGACTG |
| SEQ ID 031 | gaattgtctccctacCTAGGACTGT |
| SEQ ID 032 | aattgtctccctacCTAGGACTGTG |
| SEQ ID 033 | attgtctccctacCTAGGACTGTGA |
| SEQ ID 034 | ttgtctccctacCTAGGACTGTGAG |
| SEQ ID 035 | tgtctccctacCTAGGACTGTGAGC |
| SEQ ID 036 | gtctccctacCTAGGACTGTGAGCT |
| SEQ ID 037 | tctccctacCTAGGACTGTGAGCTG |
| SEQ ID 038 | ctccctacCTAGGACTGTGAGCTGC |
| SEQ ID 039 | tccctacCTAGGACTGTGAGCTGCC |
| SEQ ID 040 | ccctacCTAGGACTGTGAGCTGCCT |
| SEQ ID 041 | cctacCTAGGACTGTGAGCTGCCTG |
| SEQ ID 042 | ctacCTAGGACTGTGAGCTGCCTGA |
| SEQ ID 043 | tacCTAGGACTGTGAGCTGCCTGAC |

Accordingly, in various aspects of the present disclosure, morpholinos can be utilized to increase expression of sVEGFR2. The present scope includes utilizing such expression for research, clinical, diagnostic, treatment, or other beneficial uses. For example, treatment of numerous conditions in an individual are contemplated, and those skilled in the art will recognize such treatments and conditions once in possession of the present disclosure. In one aspect, for example, a method of increase expression of sVEGFR2 in a subject can generally include binding an antisense morpholino to an exon13-intron13 splicing site of gene VEGFR2. Such upregulation can be used as a treatment for various neovascularization conditions such as, for example, cancers, rheumatoid arthritis, macular degeneration, diabetic retinopathy, etc. By upregulating the expression of sVEGFR2, uncontrolled neovascularization can be brought under control and such conditions can effectively be treated. In another aspect, a method of inhibiting neovascularization in a subject is provided. Such a method can include binding an antisense morpholino to an exon13-intron13 splicing site of gene VEGFR2.

It should also be understood that the present disclosure is not limited to specific morpholino sequences, and should be inclusive of any morpholino capable of affecting alternative splicing. In one aspect, for example, the morpholino can be any morpholino that binds to a desired splicing site with a homology of greater than about 75%. One specific aspect of such a site is the exon13-intron13 splicing site.

As such, in one aspect a method of increasing expression of sVEGFR2 in a subject can include binding an antisense morpholino to an exon13-intron13 splicing site of VEGFR2 mRNA such that the VEGFR2 mRNA is spliced into an sVEGFR2 isoform. It is noted that the present scope also includes splicing sites other than the exon13-intron13 splicing site, and that any splicing site that is capable of increasing expression of sVEGFR2 due to morpholino binding is within the present scope. In addition to increasing the expression of sVEGFR2, various methods of treating VEGFR-related conditions in a subject are also considered. For example, methods of inhibiting neovascularization are also contemplated, as well as methods relating to angiogenesis, vasculogenesis, lymphangiogenesis, etc.

Sequence homology between mRNA and a given morpholino can, in some cases, be indicative of the effectiveness of splicing alteration. As such, any degree of homology between a morpholino and a VEGFR2 splice site that affects the expression of sVEGFR2 is considered to be within the present scope. In other words, in one aspect a morpholino that increases expression of sVEGFR2 in a subject is considered to have a sequence homology to the splice site that is within the present scope. In another aspect, a morpholino can bind to the splicing site with a homology of at least about 75%. In yet another aspect, a morpholino can bind to the splicing site with a homology of at least about 95%. Additionally, in other aspects a morpholino can have a sequence that is at least about 75% homologous to at least one of SEQ ID 001 to SEQ ID 043. In further aspects a morpholino can have a sequence that is at least about 95% homologous to at least one of SEQ ID 001 to SEQ ID 043. Furthermore, it is also contemplated that a morpholino sequence can be at least about 75% or at least about 95% homologous to SEQ ID 001. In a further aspect, a morpholino can have a sequence of SEQ ID 001.

In other aspects, various pharmaceutical compositions are contemplated. For example, a pharmaceutical composition for increasing expression of sVEGFR2 in a subject can include a pharmaceutically effective carrier including a morpholino capable of binding to an exon13-intron13 splicing site of VEGFR2 mRNA to facilitate increased expression of sVEGFR2. Such a composition can be utilized to treat any condition for which an increase in sVEGFR2 may be beneficial. It is noted that, while the morpholino including an oligomer selected from SEQ ID 001 to SEQ ID 043 is exemplified, any morpholino capable of facilitating an increase in sVEGFR2 is considered to be within the present scope.

It should be noted that morpholinos and morpholino compositions can be delivered to a genetic target by any known technique, depending in some cases on the nature of the target. For example, for delivery into an RNA-containing solution, morpholinos can be introduced into a buffer solution and added to the solution. For individual cells, cellular tissue, other physiological structures, or other animal or human subjects, morpholinos can be formulated with a carrier that is appropriate for the environment and the mode of delivery. Various modes of delivery are contemplated, which include, without limitation, injection, iontophoresis, passive delivery, or any other effective delivery technique. Any potential transfection technique should thus be considered to be within the present scope. One non-limiting example can include a transfection technique such as nucleofection.

Additional components are also contemplated for inclusion in a morpholino composition, and any component that provides a benefit to the delivery, storage, use, etc. of the composition is considered to be within the present scope. Additionally, such components can vary depending on the intended delivery mode utilized. Concentrations, formulation specifics, ingredient ratios, and the like can be readily determined by those skilled in the art once in possession of the present disclosure.

Figure 2:
FIG. 2 provides images showing that fluorescent morpholino can be transfected by nucleofection in accordance with another embodiment of the present invention.

Turning to FIG. 2, fluorescent conjugated morpholino can be used to confirm the transfection into human umbilical vein endothelial cells (HUVECs). FIG. 2 demonstrates that fluorescent morpholino can be transfected by nucleofection. Each morpholino of indicated amount was nucleofected into HUVECs. After 2 days, the cells were observed with fluorescence microscope. The scale bar is 100 μm.

Figure 3:
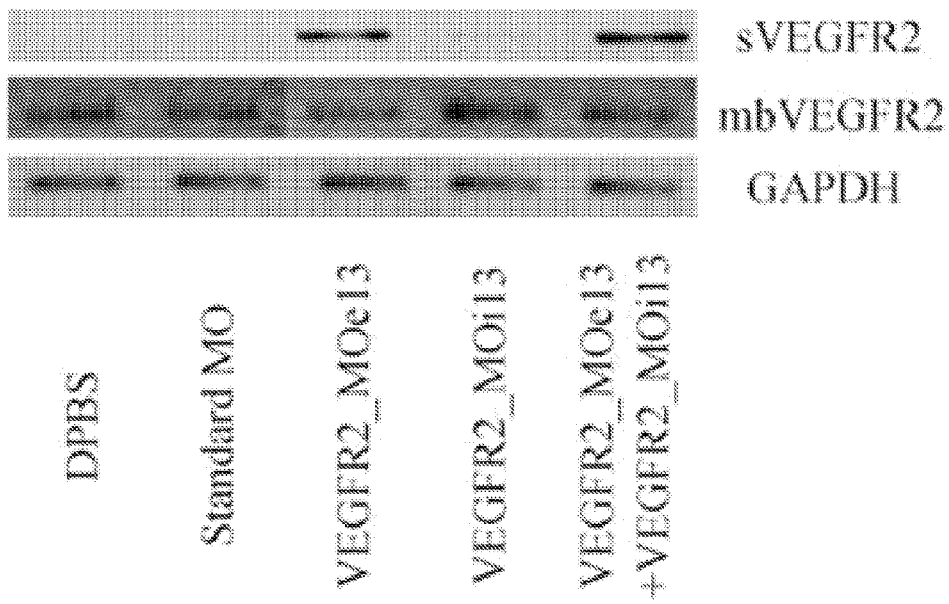
FIG. 3 shows the results of RT-PCR analysis of sVEGFR2 and mbVEGFR2 mRNA from HUVECs two days after morpholino transfection in accordance with yet another embodiment of the present invention.
Figure 4A:
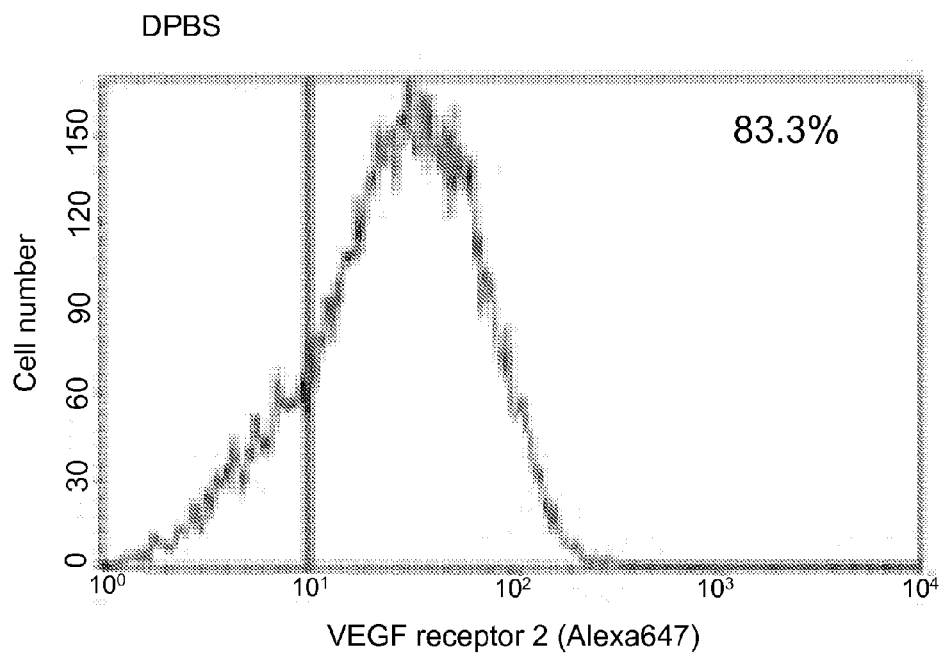
FIG. 4 shows flow cytometry analysis of mbVEGFR2 protein on cell surfaces in accordance with another embodiment of the present invention.
Figure 4B:
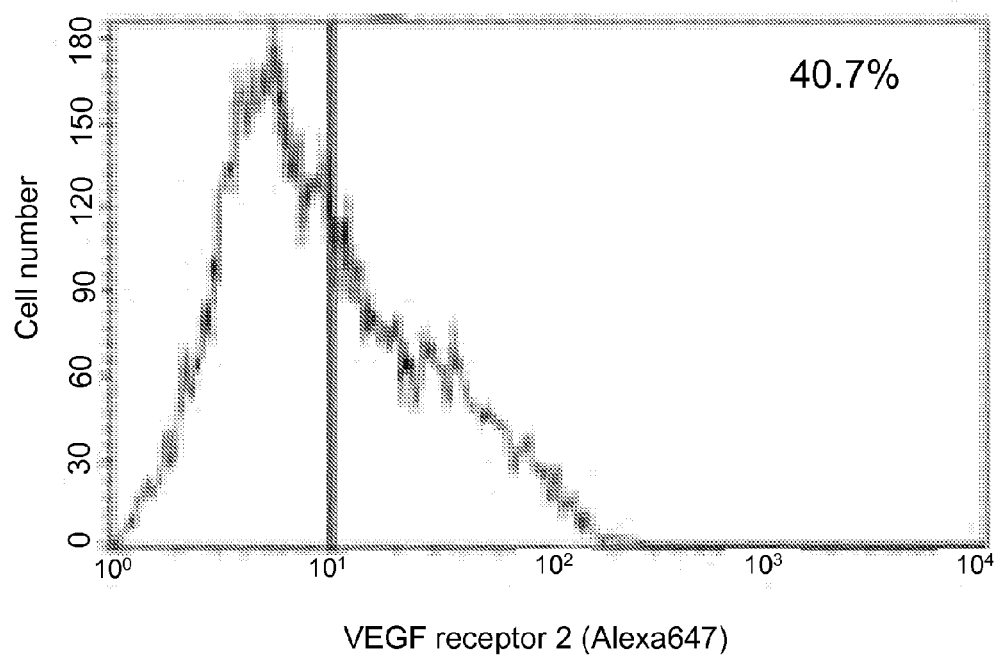
Figure 4C:
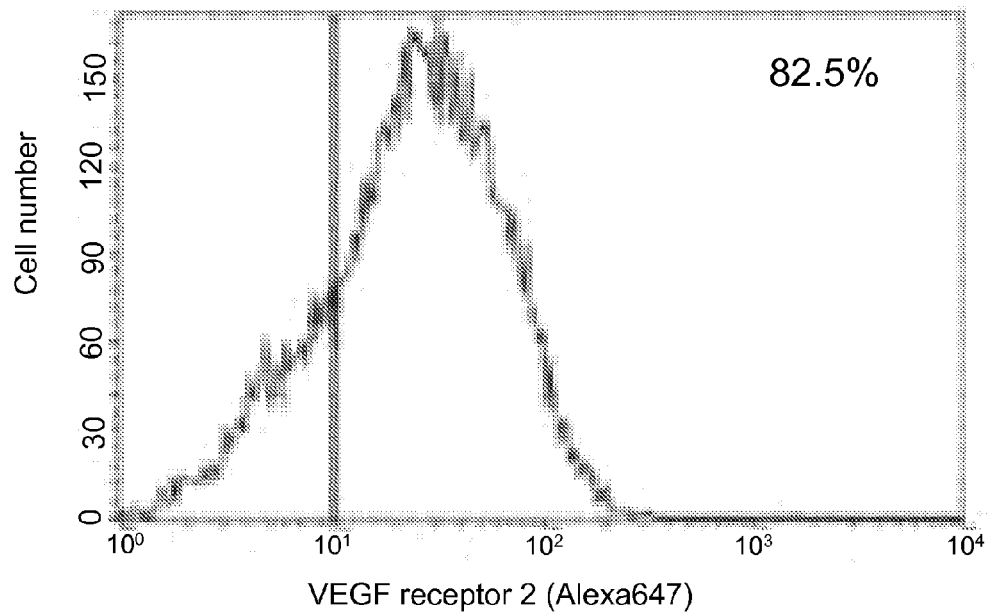
Figure 4D:
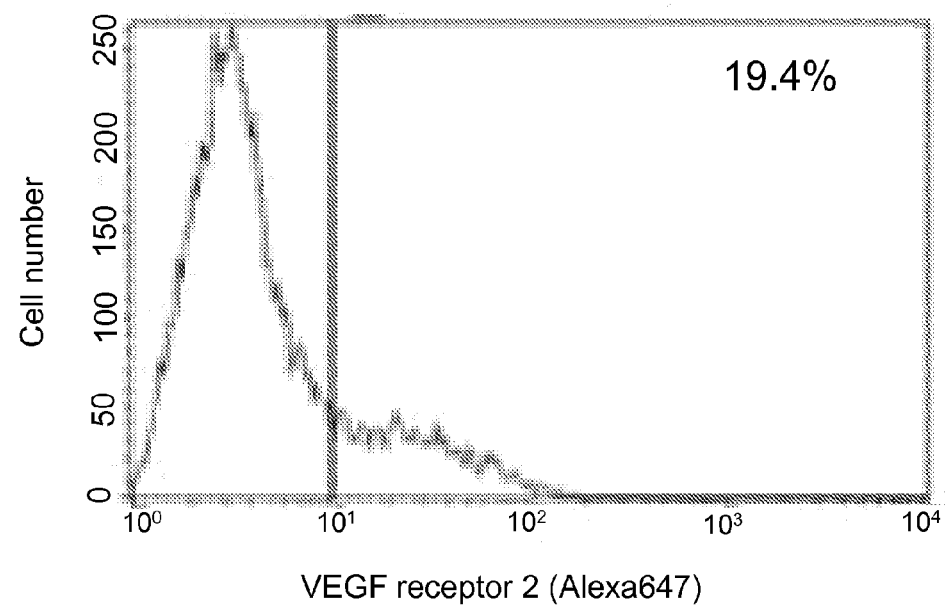
Figure 4E:
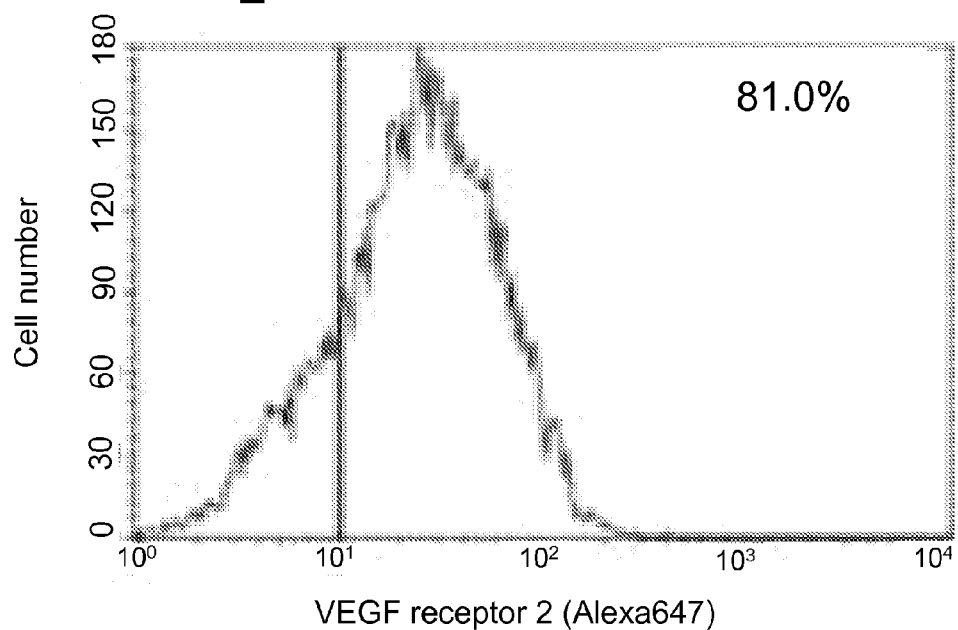
Figure 4F:
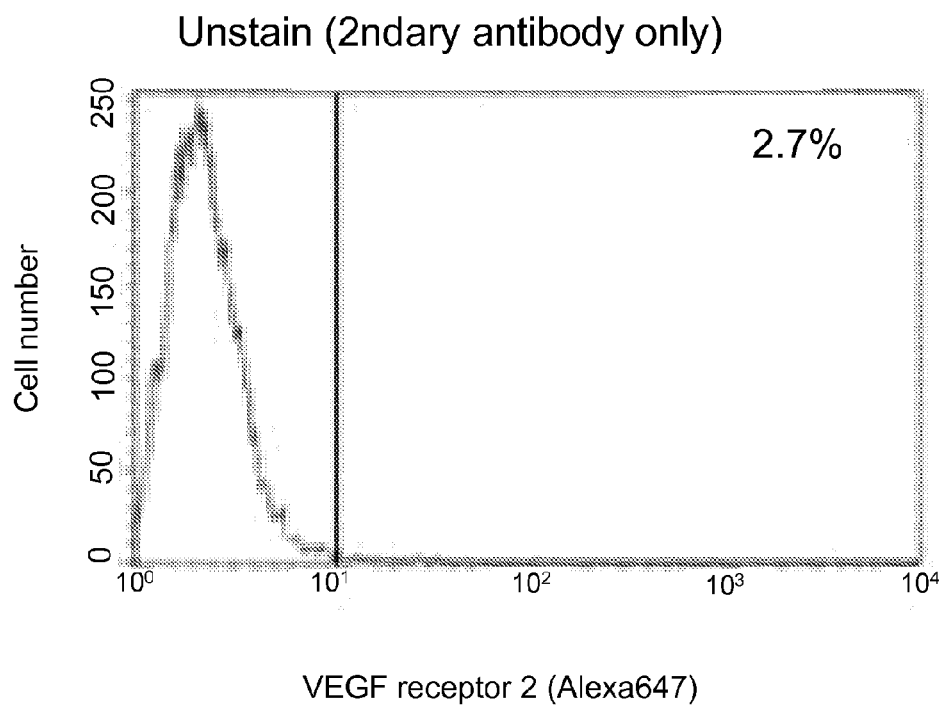

FIG. 3 shows the results of RT-PCR analysis of sVEGFR2 and mbVEGFR2 mRNA from HUVECs two days after morpholino transfection. sVEGFR2 mRNA is detected in HUVECs transfected with VEGFR2_MOe13, VEGFR2_MOi13 and the combination of VEGFR2_MOe13 and VEGFR2_MOi13. In Dulbecco's Phosphate-Buffered Saline (DPBS) or standard morpholino (STD_MO) transfected HUVECs, sVEGFR2 mRNA is detected only at higher PCR cycles (data not shown). FIG. 3 shows RT-PCR results for sVEGFR2 and mbVEGFR2 in each subgroup of morpholino transfected HUVECs. To limit the possibility of genomic contamination, VEGFR2exon10_F (designed in exon10) and VEGFR2_R (designed in intron13) were used for primers to detect sVEGFR2. In DPBS or STD_MO transfected HUVECs, sVEGFR2 mRNA was detected only at higher PCR cycles.

To quantify these results, real-time PCR can be performed using glyceraldehyde-3-phosphate dehydrogenase (GAPDH) as an internal control (See FIGS. 1B-C) It was discovered that VEGFR2_MOe13 downregulates mbVEGFR2 mRNA by 40% (p<0.05), while VEGFR2_MOi13 upregulates mbVEGFR2 mRNA by 2.5-fold (p<0.01) compared with DPBS transfected HUVECs. A combination of VEGFR2_MOe13 and VEGFR2_MOi13 does not alter mbVEGFR2 mRNA when compared to DPBS transfected HUVECs. In contrast to mbVEGFR2 mRNA, sVEGFR2 mRNA shows a 17-fold increase (p<0.001) with VEGFR2_MOe13, a 4.4-fold increase (p<0.001) with VEGFR2_MOi13, and a 35-fold increase (p<0.001) with the VEGFR2_MOe13 and VEGFR2_MOi13 combination, respectively.

Figure 5A:
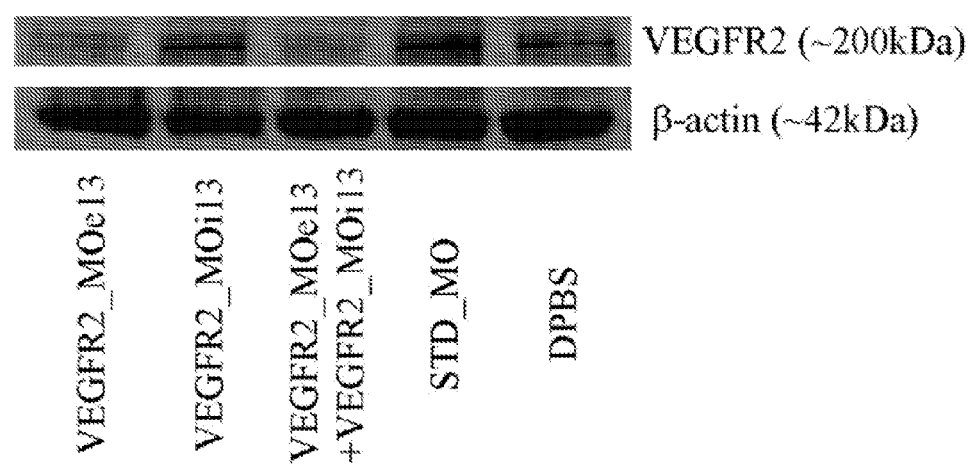
FIG. 5 shows that VEGFR2_MOe13 decreases mbVEGFR2 protein and increases sVEGFR2 protein in accordance with another embodiment of the present invention.
Figure 5B:
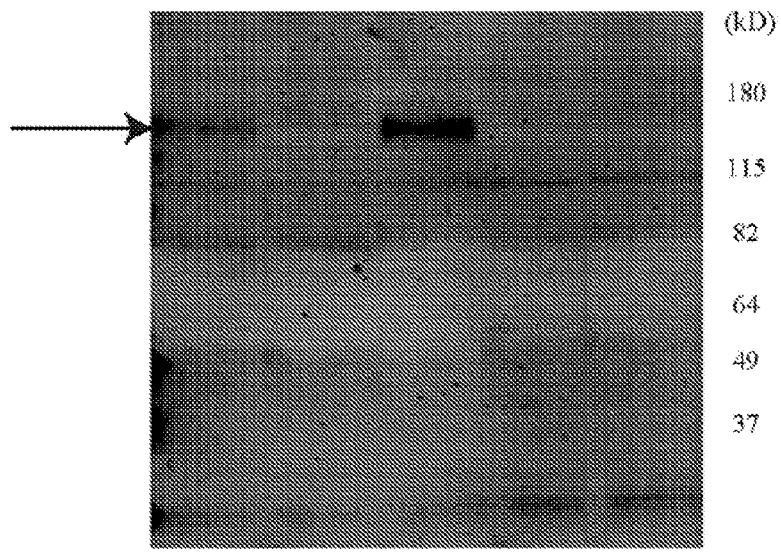
Figure 5C:
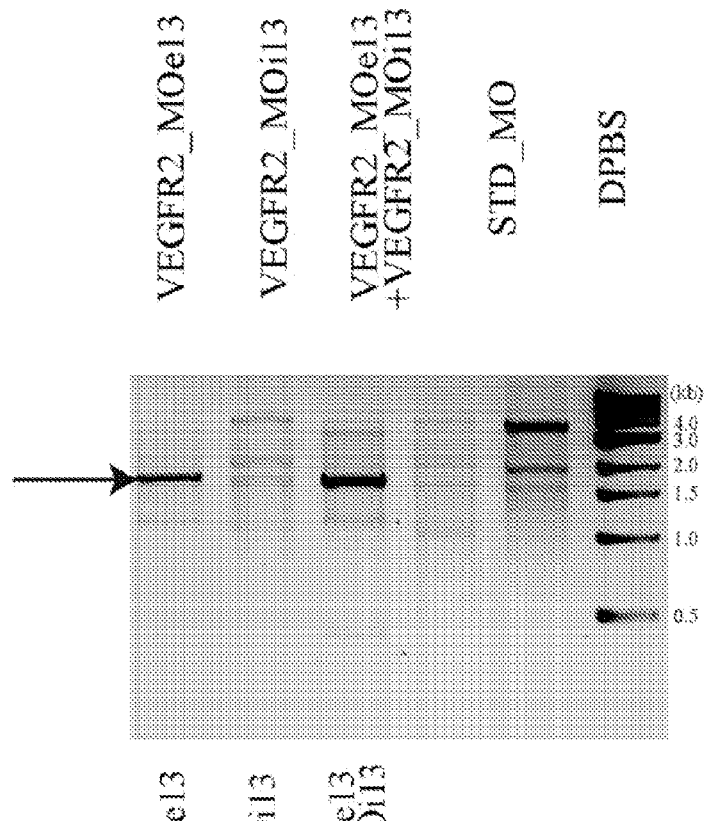

Next, mbVEGFR2 protein expression by western blot was examined. VEGFR2_MOe13 or a combination of VEGFR2_MOe13 and VEGFR2_MOi13 reduced mbVEGFR2 protein expression compared to DPBS and STD_MO. On flow cytometry, DPBS and STD_MO transfected HUVECs, 83.3% and 81.0% were mbVEGFR2 positive, respectively, while VEGFR2_MOe13 decreased mbVEGFR2 positive cells to 40.7% (FIG. 4). FIG. 4 shows flow cytometry analysis of mbVEGFR2 protein on cell surfaces, with (a) DPBS, (b) VEGFR2_MOe13, (c) VEGFR2_MOi13, (d) VEGFR2_MOe13 and i13, (e) STD_MO transfected HUVECs. (f) HUVECs stained with only secondary antibody were used as a negative control. The combination of VEGFR2_MOe13 and VEGFR2_MOi13 reduced mbVEGFR2 positive cells to 19.4%. HUVECs transfected with only VEGFR2_MOi13 showed similar percentages of VEGFR2 positive cells (82.5%) to the controls, despite real-time PCR data showing an increase of mbVEGFR2 mRNA. Thus, this data demonstrates that VEGFR2_MOe13 strongly inhibits mbVEGFR2 protein expression. By contrast, VEGFR2_MOi13 showed an additive effect only in the presence of VEGFR2_MOe13. To confirm sVEGFR2 protein expression, western blot from culture medium of morpholino transfected HUVECs was performed using an antibody recognizing the extracellular domains of VEGFR2 (FIG. 5). FIG. 5 shows that VEGFR2_MOe13 decreases mbVEGFR2 protein and increases sVEGFR2 protein. FIG. 5(a) shows a Western blot for mbVEGFR2 from each morpholino transfected HUVEC. FIG. 5(b) shows Western blot of culture medium against VEGFR2 extracellular domain. FIG. 5(c) Shows agarose electrophoresis image of long range 3'RACE showed an up-regulation of approximately 1600 bp band upon administering, both, VEGFR2_MOe13 and the combination of VEGFR2_MOe13 and i13. Although the calculated molecular weight of human sVEGFR2 is approximately 76 kD, 150 kD bands were detected in the culture medium of HUVEC transfected with VEGFR2_MOe13 and the combination of VEGFR2_MOe13 and i13. It is known that mbVEGFR2 can be glycosylated, thus increasing the molecular weight from 150 kD to 230 kD. In addition, sVEGFR2 has been detected at 160 kDa, although it has not reported whether this was derived from alternative polyadenylation or proteolytic cleavage from mbVEGFR2. Based on this information, it is likely that sVEGFR2 protein, upregulted following morpholino treatment, is glycosylated with an observed molecular weight of 150 kDa.

Figure 6A:
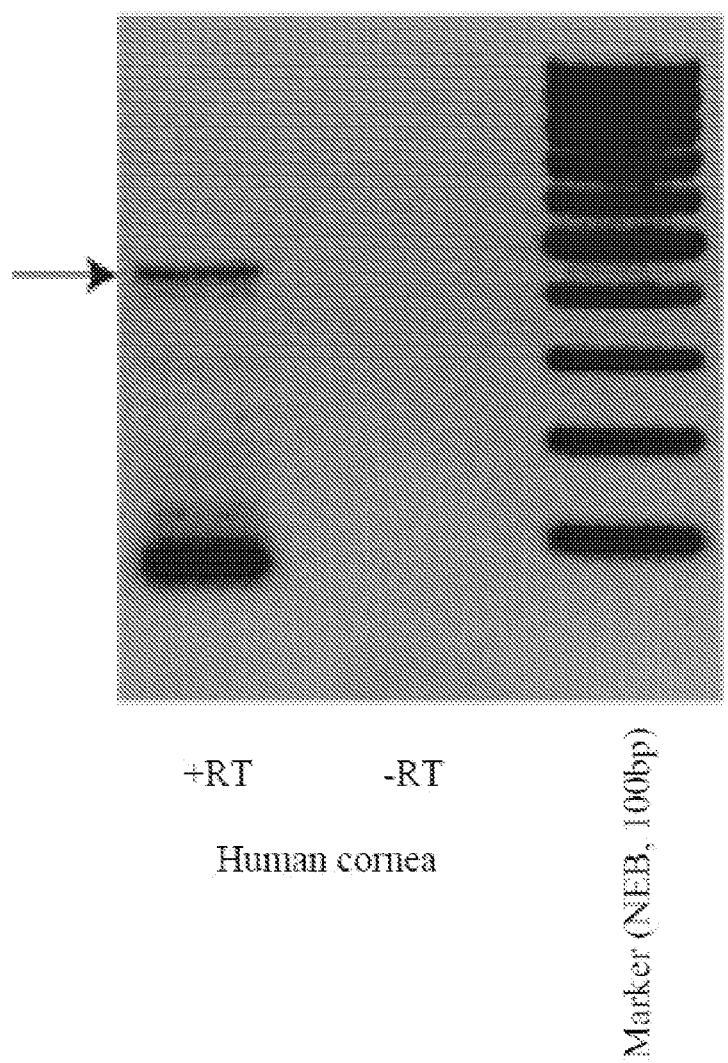
FIG. 6 shows that VEGFR2_MOe13 activates the polyadenylation site that is used for sVEGFR2 mRNA in human cornea in accordance with another embodiment of the present invention.
Figure 6B:
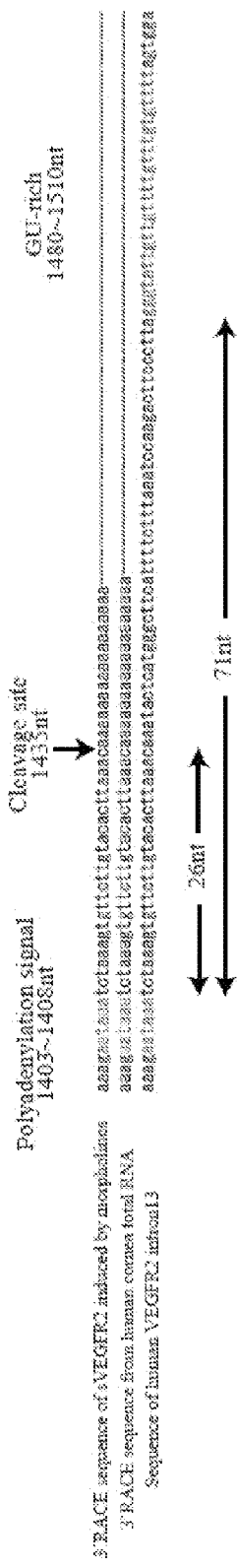

To determine the 3'UTR of sVEGFR2 mRNA induced by morpholinos, longrange 3'RACE was performed (FIG. 5C). A strong band (~1600 bp) was detected from VEGFR2_MOe13 and the combination of VEGFR2_MOe13 and VEGFR2_MOi13 transfected HUVECs. Based on the sequence of this band, sVEGFR2 mRNA utilizes a polyadenylation site located in 1403~1408 nt range of intron13 (FIG. 6B). FIG. 6 shows VEGFR2_MOe13 activates the polyadenylation site that is used for sVEGFR2 mRNA in human cornea. FIG. 6(a) demonstrates that 3'RACE showed a single band from human cornea cDNA. FIG. 6(b) Shows a sequence results of 3'RACE products. sVEGFR2 mRNA that is induced with VEGFR2_MOe13 utilizes the same polyadenylation site as in sVEGFR2 mRNA of human cornea. The sequence of the 3'RACE product indicates that a cleavage site (CA dinucleotides) and a GU-rich region are located 26 nt and 71 nt downstream of AAUAAA, respectively. These sequence components are similar to typical polyadenylation signals, which contain a cleavage site 10-35 nt downstream of AAUAAA and a GU-rich region 14-70 nt downstream of AAUAAA. Based on this result, the inventors sought to identify the 3'UTR of sVEGFR2 from human corneal total RNA (FIG. 6A). Corneal tissue is known to predominantly express sVEGFR2. It was found that in the human cornea, sVEGFR2 mRNA utilizes the same polyadenylation site which the current morpholinos induced (FIG. 6B).

Figure 7A:
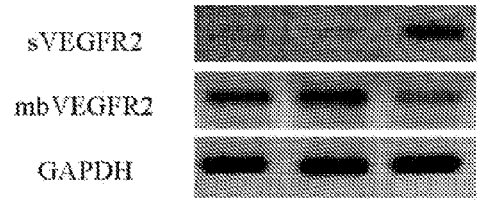
FIG. 7 shows that moVEGFR2_MOe13 suppresses experimental neovascularization and lymphangiogenesis in mouse in accordance with another embodiment of the present invention.
Figure 7B:
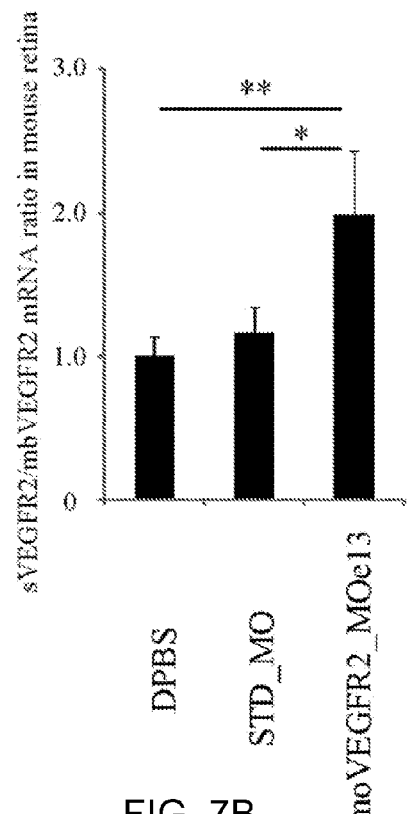
Figure 7C:
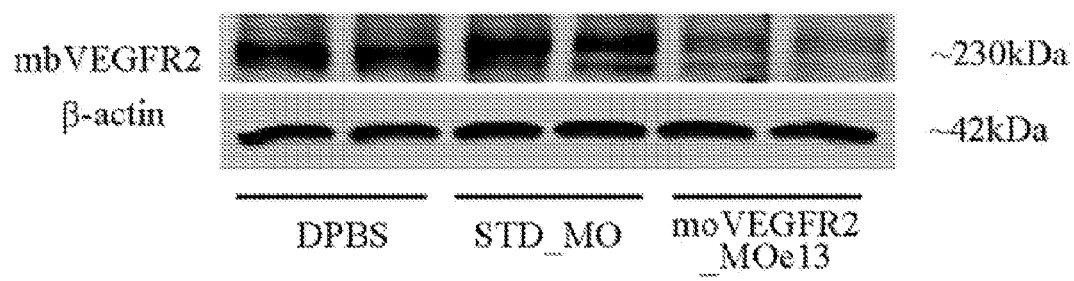
Figure 7D:
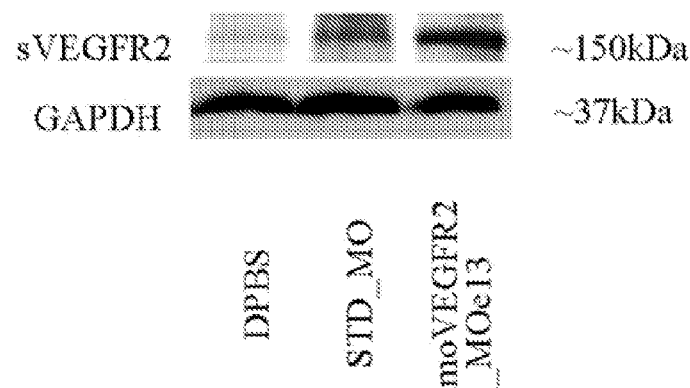
Figure 7G:
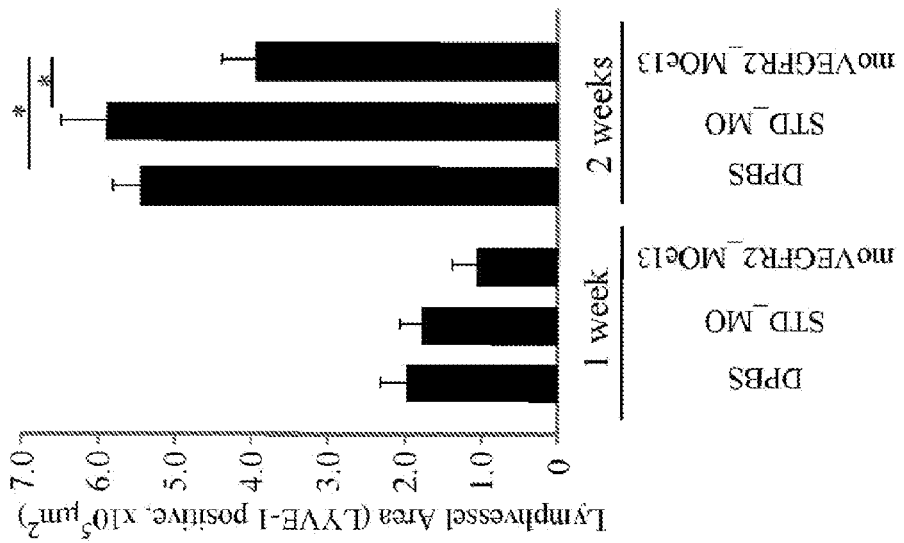
Figure 7F:
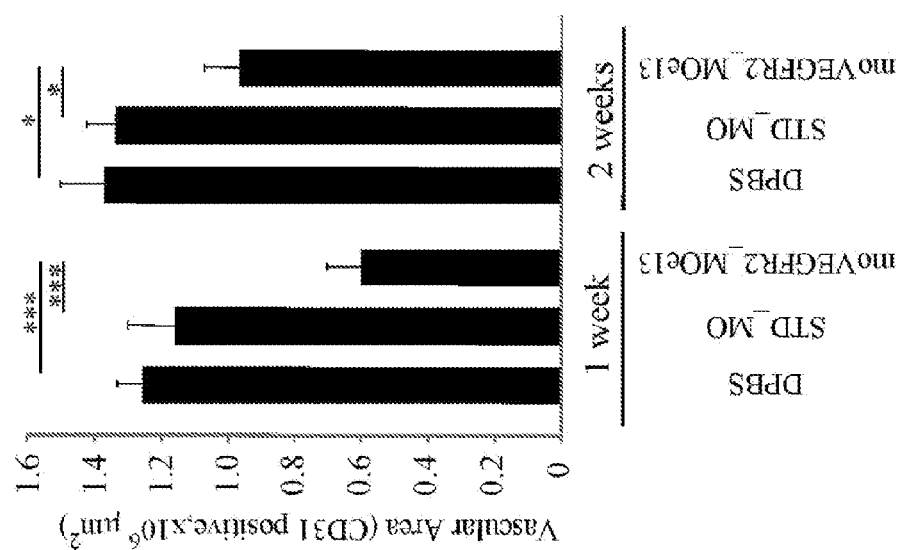
Figure 7E:
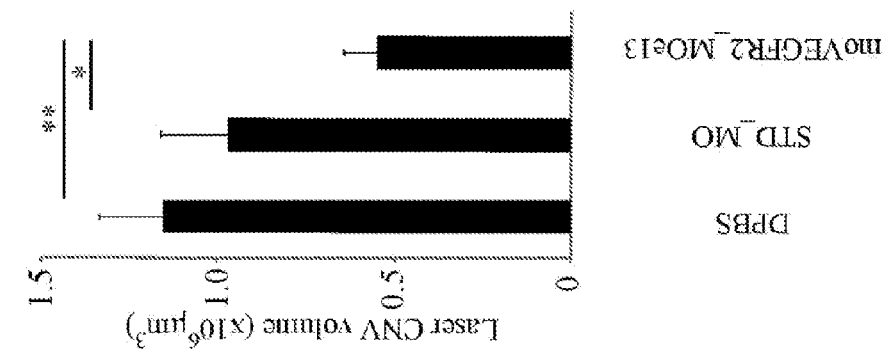

Because VEGFR2_MOe13 decreases mbVEGFR2 and increases sVEGFR2, it is expected that VEGFR2_MOe13 can inhibit angiogenesis and lymphangiogenesis in vivo. To study the effect of VEGFR2_MOe13 in animal models, moVEGFR2_MOe13 was created that targets the exon13-intron13 junction of the mouse VEGFR2 gene. By RT-PCR analysis, it was found moVEGFR2_MOe13 increased sVEGFR2 mRNA and decreased mbVEGFR2 mRNA in the mouse MS-1 cell line (FIG. 7A). FIG. 7 shows that moVEGFR2_MOe13 suppresses experimental neovascularization and lymphangiogenesis in mouse. FIG. 7(a) shows RT-PCR results for sVEGFR2 and mbVEGFR2. FIG. 7(b) shows sVEGFR2/mbVEGFR2 ratio in mouse retina after injection intravetrously was determined by quantitative real-time PCR (each group, n=4). FIG. 7(c) shows a Western blot for mbVEGFR2 from mouse retinal protein. FIG. 7(d) shows a Western blot for sVEGFR2 from mouse ocular solution. FIG. 7(e) shows the average of laser-induced CNV (n=11-17). FIG. 7(f, g) show the mean area of corneal neovascularization and lymphangiogenesis respectively (n=13-16). Risk factors (p-value) were calculated by two-tail student's t-test (*:$p<0.05$, $p<0.01$, *$p<0.001$). Error bar is ±s.e.m.

To administer morpholinos in vivo, morpholino conjugated with a dendrimer at the 3' position (vivo-morpholino) was used for animal experiments. It should be understood that this technique is merely exemplary, and any other method of administration is considered to be within the present scope. To determine whether moVEGFR2_MOe13 works in vivo, each morpholino or DPBS was injected intravitreously and the retinal total RNA was subjected to real-time PCR for sVEGFR2 and mbVEGFR2 mRNA (FIG. 7B). moVEGFR2_MOe13 significantly increased sVEGFR2/mbVEGFR2 mRNA ratio. Next, the protein level of mbVEGFR2 and sVEGFR2 in the retina and the ocular solution was examined by western blot. Consistent with real-time PCR results, moVEGFR2_MOe13 decreased mbVEGFR2 protein in the retina (FIG. 7C) and increased sVEGFR2 protein in the ocular solution (FIG. 7D).

Figure 8:
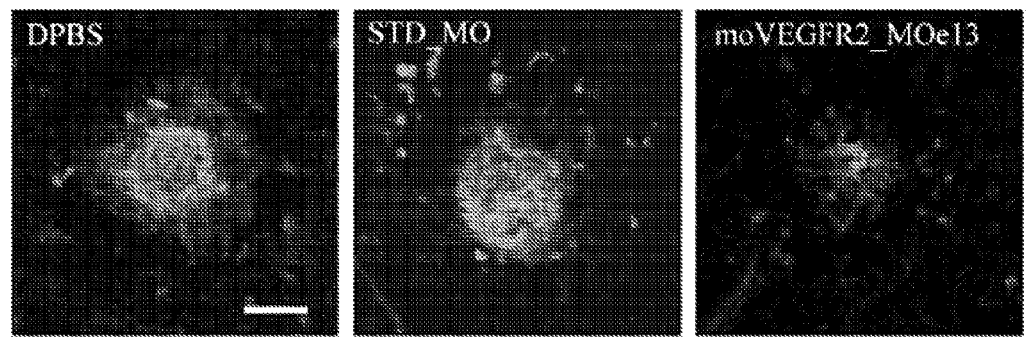
FIG. 8 shows representative images of laser induced CNV in accordance with another embodiment of the present invention.
Figure 9:
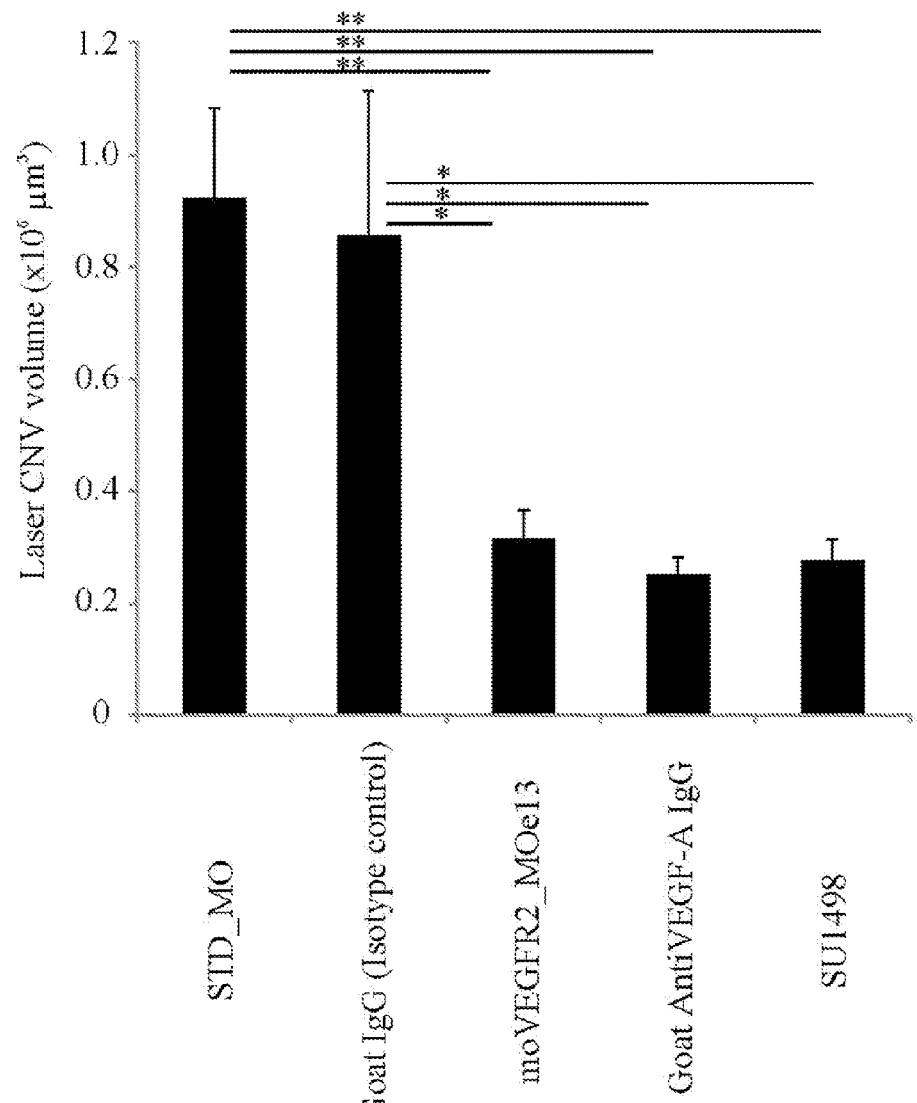
FIG. 9 shows moVEGFR2_MOe13 suppression of CNV is comparable to inhibitory effects of anti-VEGF antibody or VEGFR2 tyrosine kinase inhibitor in accordance with another embodiment of the present invention.

It was also examined whether moVEGFR2_MOe13 inhibits laser-induced choroidal neovascularization (CNV). Each morpholino or DPBS was injected intravitreously on day 1 and day 4 after laser photocoagulation, and laser CNV volumes were examined on day 7. FIG. 8 shows representative images of laser CNV with DPBS, STD_MO and moVEGFR2_MOe13. FIG. 8 shows representative images of laser induced CNV. Vessel endothelial cells were stained with Alexa fluor488 conjugated isolectin GS-IB4. The scale bar is 100 µm. moVEGFR2_MOe13 significantly suppressed laser CNV volume compared with STD_MO ($p<0.05$) and DPBS ($p<0.01$) (FIG. 3E). In addition, moVEGFR2_MOe13 treatment was comparable to anti-VEGF-A IgG and VEGFR2 kinase inhibitor (SU1498) treatment (FIG. 9). Morpholinos may have potential advantages of reduced molecular weight and immunogenicity compared to antibodies and higher specificity compared to small molecules FIG. 9 shows moVEGFR2_MOe13 suppression of CNV is comparable to inhibitory effects of anti-VEGF antibody or VEGFR2 tyrosine kinase inhibitor. After photocoagulation, on day 1 and day 4, 2 ul of 100 ng/µl STD_MO, 500 ng/µl Goat IgG (AB-108-C, R&D Systems. Minneapolis, Minn.), 100 ng/µl moVEGFR2_MOe13, 500 ng/µl Goat Anti-mouse VEGF-A IgG (AF-493-NA, R&D Systems, Minneapolis, Minn.) or 2 ng/µl SU1498 (572888, EMD chemicals, Gibbstown, N.J.) was injected intravitreously. On day 7, CNV volumes were measured by confocal microscope. n=14-20 for each group. Risk factors (p-value) were calculated by two-tail student's t-test (*:$p<0.05$, **$p<0.01$). Error bar is ±s.e.m.

Figure 10:
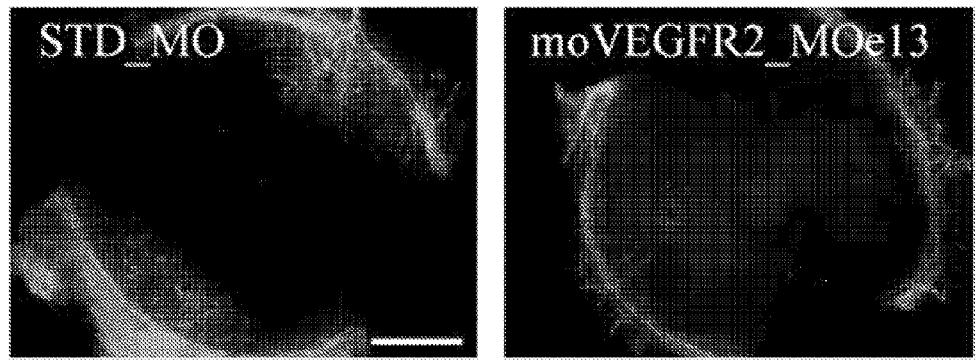
FIG. 10 shows representative images of CD31 stained corneas at one week in accordance with another embodiment of the present invention.
Figure 11:
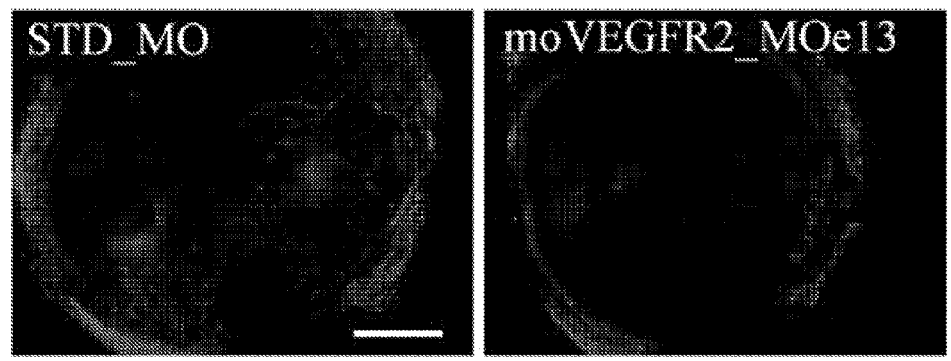
FIG. 11 shows representative images of LYVE-1 stained corneas at two weeks in accordance with another embodiment of the present invention.

In another aspect, a corneal suture model can be used to evaluate angiogenesis. For the one week subarm, each morpholino or DPBS was injected subconjunctivally one day prior to and four days after suturing; the corneas were harvested at seven days post suturing. For the two week subarm, each morpholino or DPBS was injected subconjunctivally one day prior to and four, seven and ten days after suturing; the corneas were harvested at fourteen days. CD31 and LYVE-1 were used as markers of neovascularization and lymphangiogenesis, respectively. FIGS. 10 and 11 representative images of CD31 stained corneas at one week and LYVE-1 stained corneas at two weeks, respectively. FIGS. 7F-G display the mean area of neovascularization and lymphangiogenesis in each group. moVEGFR2_MOe13 suppressed suture-induced neovascularization by 52.2% (1 week) and 29.6% (2 weeks) compared to DPBS ($p<0.001$ and 0.05, respectively). One week after suture placement, moVEGFR2_MOe13 did not suppress lymphangiogenesis. However, 2 weeks after suture placement, moVEGFR2_MOe13 suppressed lymphangiogenesis by 27.8% compared to DPBS ($p<0.05$).

Figure 12:
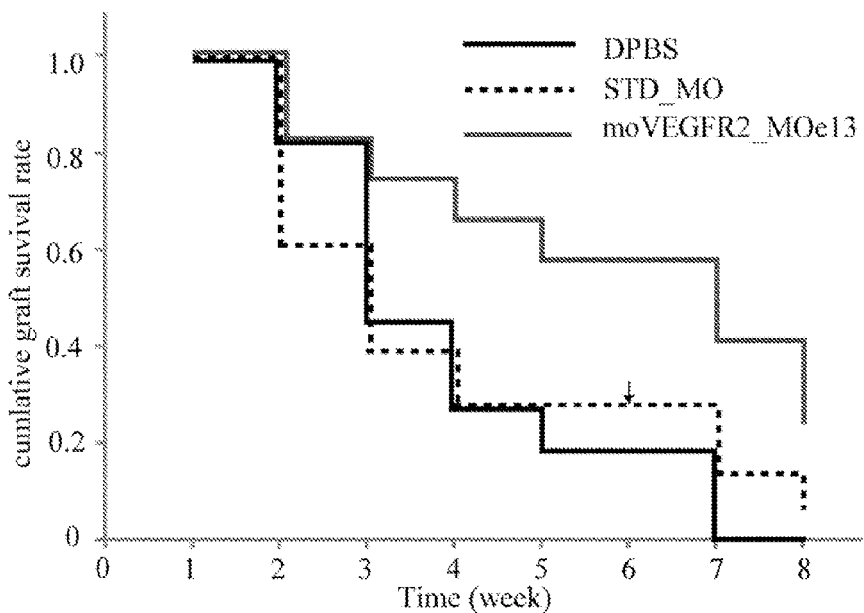
FIG. 12 shows that moVEGFR2_MOe13 suppresses rejection in mouse cornea transplantation model in accordance with another embodiment of the present invention.
Figure 12B:
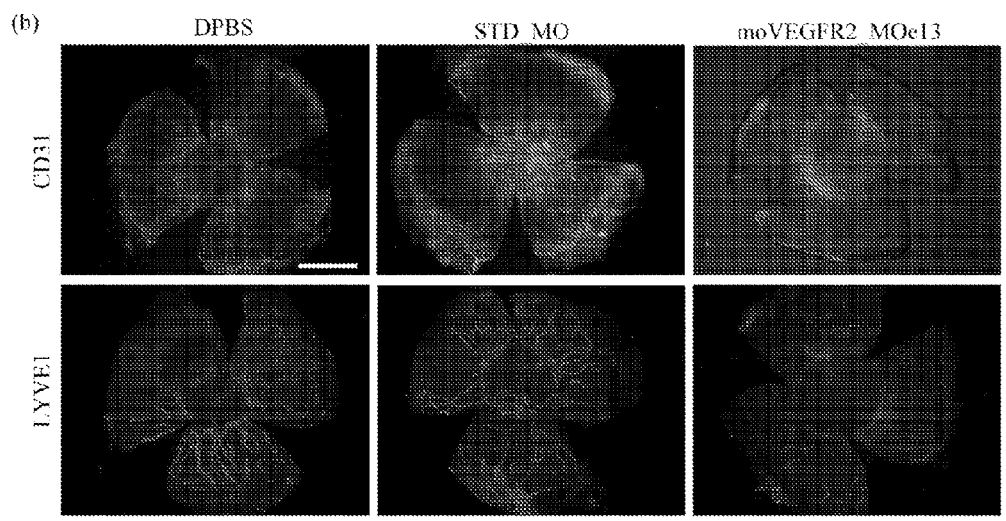
Figure 12C:
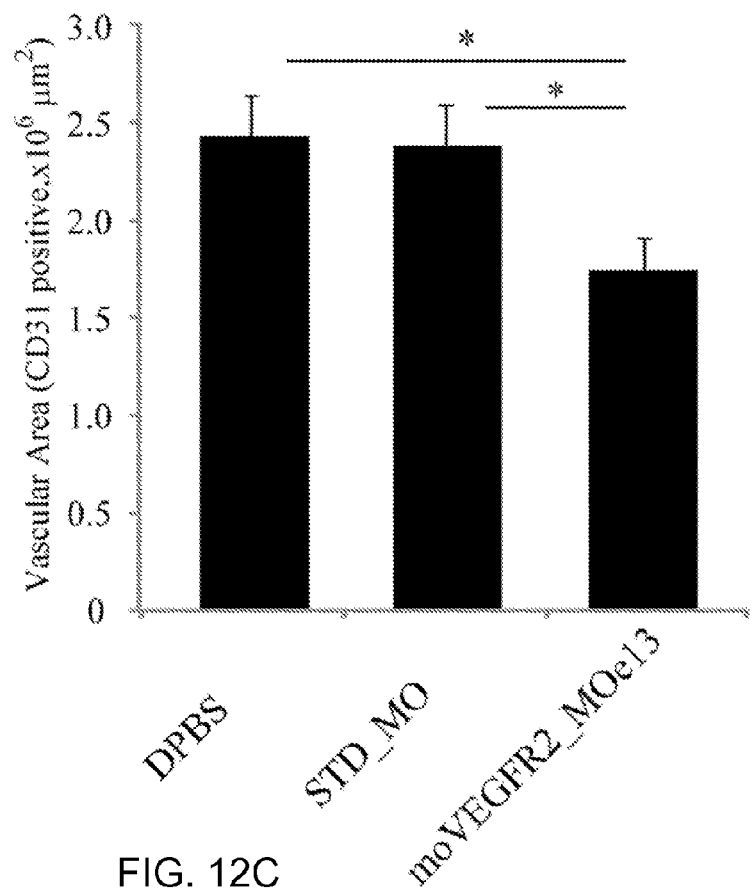
Figure 12D:
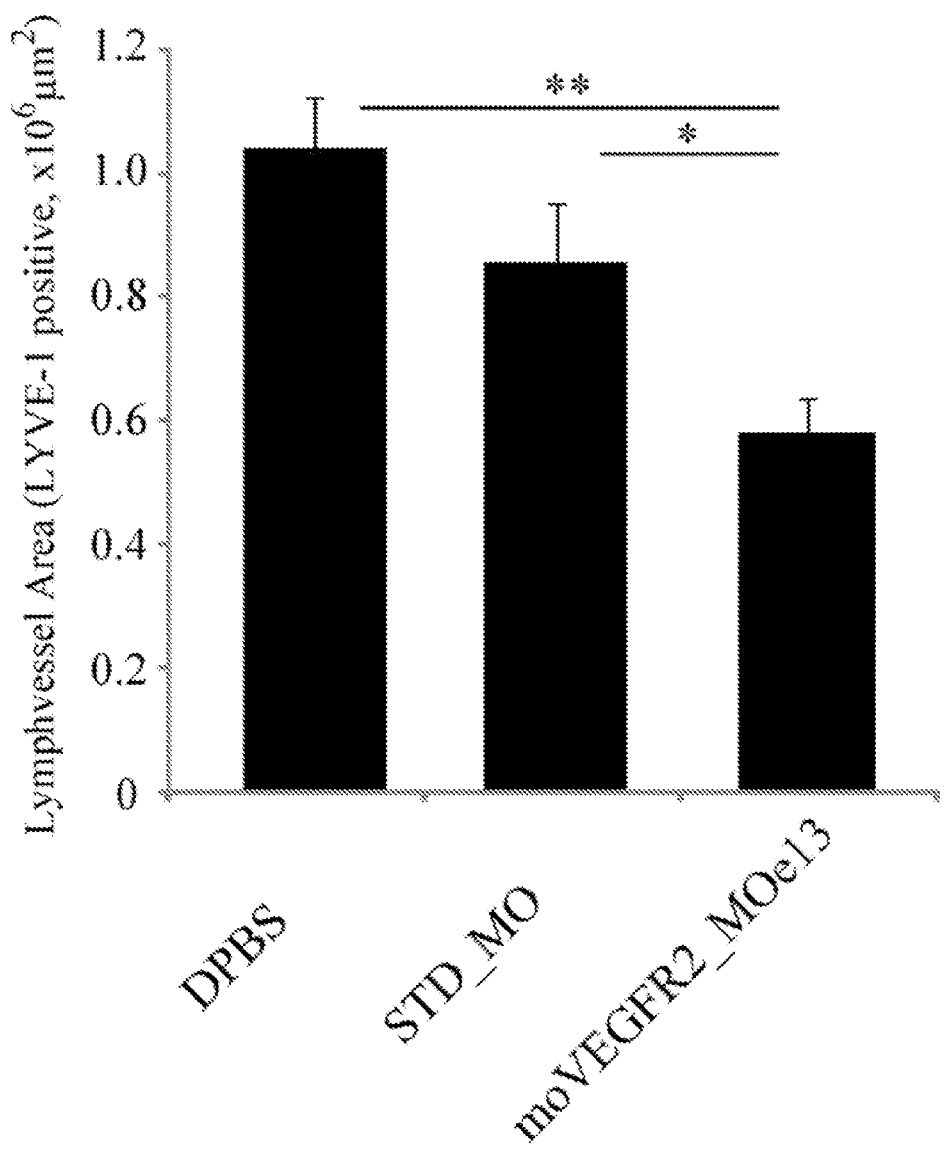

It was also examined whether moVEGFR2_MOe13 can suppress murine corneal transplant rejection. After cornea transplantation, moVEGFR2_MOe13, STD_MO or DPBS were injected subconjuctivally. It was found that moVEGFR2_MOe13 increased graft survival compared with DPBS and STD_MO (FIG. 12A, log rank test: p=0.0186 and 0.0610, respectively). FIG. 12B shows the representative images of CD31 and LYVE-1 stained cornea at the endpoint (8 weeks). Concordantly, in a model of cornea suture injury model, moVEGFR2_MOe13 decreased neovascularization and lymphangiogenesis significantly (FIGS. 12C, D). FIG. 12 shows that moVEGFR2_MOe13 suppresses rejection in mouse cornea transplantation model. FIG. 12(a) shows cumulative graft survival rate. moVEGFR2_MOe13 increased graft survival rate compared with DPBS and STD_MO (log rank test: p=0.0186 and 0.0610, respectively). The arrow indicates censored data. FIG. 12(b) Shows a representative image of corneal neovascularization and lymphangiogenesis at 8 weeks. Scale bar is 1 mm. FIG. 12(c, d) Show the mean area of corneal neovascularization and lymphangiogenesis at 8 weeks respectively (n=11-17). Risk factors (p-value) were calculated by two-tail student's t-test (*:$p<0.05$, **$p<0.01$). Error bar is ±s.e.m.

It is thus demonstrated that the latent polyadenylation site in intron13 of VEGFR2 can be activated by blocking the upstream 5'splicing site (exon13-intron13 junction) using VEGFR2_MOe13, which decreased mbVEGFR2 and increased sVEGFR2 at mRNA and protein levels. However, blocking the 3'splicing site (intron13-exon14 junction) using VEGFR2_MOi13 increased mbVEGFR2 and sVEGFR2 mRNA but not protein. The reason is unclear, but truncated or incompletely processed RNA may be induced by VEGFR2_MOi13. In addition, 3'RACE from VEGFR2_MOi13 transfected HUVECs did not show a strong band corresponding to sVEGFR2 mRNA using the polyadenylation site in intron13, and we could not detect sVEGFR2 protein from culture medium of HUVECs transfected with VEGFR2_MOi13. This validates the idea that VEGFR2_MOi13 induces truncated or unprocessed RNA and VEGFR2_MOe13 is responsible for activating the polyadenylation site. The combination of VEGFR2_MOe3 and VEGFR2_MOi13 was more effective than VEGFR2_MOe13 treatment alone at modifying RNA and protein expression of mbVEGFR2 and sVEGFR2. Thus, blocking both upstream and downstream splice sites more effectively induces the polyadenylation signal.

The polyadenylation signal induced by morpholino is normally inactive in HUVECs, preferentially excluding intron13 during physiologic splicing. VEGFR2_MOe13 likely competes with U1snRNPs at the exon13-intron13 junction. U1snRNPs may inhibit downstream polyadenylation signals and are one of the key components for the splicing event although U1snRNP-independent RNA splicing has been demonstrated. It is probable that VEGFR2_MOe13 activates the latent polyadenylation signal by inhibiting U1snRNPs binding to the exon13-intron13 junction.

A novel concept is thus demonstrated of activating a latent polyadenylation signal using morpholino oligomers. This has applications not only for anti-angiogenesis by targeting VEGFR2 but in other conditions where regulatory manipulation of splicing and polyadenylation could have therapeutic valence.

Numerous methods of use for the latent polyadenylation system are contemplated, and any such use is considered to be within the present scope. Non-limiting examples of such uses can include various cancer conditions, ocular conditions, rheumatoid arthritis, and any other conditions whereby a morpholino is capable of affecting latent polyadenylation to produce a beneficial effect. Numerous physiological effects can thus be generated depending on the target site of such a procedure. Non-limiting examples of cancer conditions can include breast cancer, colon cancer, lymphoma, prostate cancer, leukemia, and the like. Non-limiting examples of ocular conditions include diabetic retinopathy, macular degeneration, and the like. For example, the anti-sense morpholino oligomer directed against the exon13-intron13 junction that increases sVEGFR2 and decreases mbVEGFR2 from the VEGFR2 gene can be used to treat various ocular conditions. Essentially, this can achieve steric blocking of the spliceosome from interacting with the junction where splicing begins which shifts mKDR to sKDR. For other genes, the splicing junction may be a different junction which can be similarly targeted. In one aspect relating to ocular delivery, morpholino injection into the intravitreous cavity can suppress laser choroidal neovascularization (CNV) while increasing sVEGFR2 in the intravitreous cavity. Furthermore, in a mouse corneal suturing model, injection of the morpholino into the subconjunctival space suppresses corneal angiogenesis and lymphangiogenesis, and suppresses graft rejection in mouse corneal transplantation model. Exon/intron recognition by splicing factors affects polyadenylation signal activation; morpholino modulation of latent polyadenylation signals can induce alternative intron retention and expression of different protein isoforms. It is clear, therefore, that modulation of alternative polyadenylation can be therapeutically useful.

It should be noted that a morpholino composition can be administered to a subject by any known technique, and any such delivery pathway is considered to be within the present scope. Non-limiting examples can include oral compositions, injectable compositions, topical compositions, iontophoretic compositions, and the like, including combinations thereof.

Methods Summary

Each morpholino oligomer was purchased from Gene Tools (Philomath, Oreg.). The sequences of each morpholino oligomer and primers for PCR are listed in supplemental Table. HUVECs (Lonza, Walkersville, Md.) were cultured in EBM with EGM SingleQuot Kit supplements and growth factors according to the manufacturer's instructions (Lonza, Walkersville, Md.). MS-1 cells, a mouse endothelial cell line (ATCC, Manassas, Va.) were cultured in 5% FBS/DMEM. Morpholino oligomers were delivered to the nucleus by nucleofection (Amaxa, Gaithersburg, Md.) with a Basic Nucleofector Kit for Primary Mammalian Endothelial Cells (Amaxa, Gaithersburg, Md.) using program A-034 for HUVEC and MS-1 cells. For each nucleofection, $1 \times 10^6$ cells were used and plated on a 6-well plate. After 2 days of culture, cells were trypsinized and total RNA was extracted using a RNeasy mini kit (Qiagen, Valencia, Calif.) with DNaseI treatment. Detection of mbVEGFR2 was achieved by flow cytometry. Three days after nucleofection, cells were treated with trypsin-EDTA and incubated in mouse anti-VEGFR2 antibody (ab9530, 1:1000, Abcam, Cambridge, Mass.) with 10% FBS and 1% sodium azide/PBS for 60 minutes. After three washes in PBS, the cells were incubated in Alexa Fluor® 647 conjugated anti-mouse IgG antibody (Invitrogen Corporation, Carlsbad, Calif.) for 30 minutes. The cells were washed three times and fluorescence was detected by a FACScan Analyzer (BD Biosciences, San Jose, Calif.). Balb/c mice and C57BL6 mice were obtained from The Jackson Laboratory (Bar Harbor, Me.). Laser photocoagulation, intravitreous injection and CNV measurement were described previously and the conditions are described in FIG. 13.

Additional Methods

Complementar, DNA (cDNA) Synthesis and Quantification with Real-Time PCR cDNAs were synthesized from 400 ng total RNA using Omniscript RT kit (Qiagen, Valencia, Calif.) and Oligo-dT primer (dT20) according to the manufacturer's instructions. Real-time PCR was performed using QuantiTect SYBR Green PCR Kit (Qiagen, Valencia, Calif.) and 1 µl of cDNA. The primer sequences were listed in Table 1. The combination of VEGFR2_F1 and R1, VEGFR2_F3 and R1, or moVEGFR2_F1 and R1 were designed to detect human and mouse sVEGFR2, respectively. The combination of VEGFR2_F2 and R2 or moVEGFR2_F2 and R2 were designed to detect human and mouse mbVEGFR2, respectively. Real-time PCR conditions: 50° C. for 2 minutes, 95° C. for 10 minutes, followed by 40 cycles of 94° C. for 15 seconds, 55° C. for 30 seconds, and 72° C. for 30 seconds.

3'RACE (Rapid Amplification of cDNA Ends)

cDNA was synthesized from total RNA extracted from morpholino transfected HUVEC using a cloning_R1 (Table 1). PCR was performed using a LongRange PCR Kit (Qiagen, Valencia, Calif.). PCR conditions: 93° C. for 3 minutes, 35 cycles of 93° C. for 15 seconds, 55° C. for 30 seconds and 68° C. for 6 minutes using VEGFR2_F1 and cloning_R2. After 1% agarose gel electrophoresis, specific bands were excised and subjected to DNA sequencing. To determine endogenous 3'UTR of sVEGFR2 mRNA, total RNA extracted from one human cornea which was obtained from the Utah Lions Eye Bank. cDNA was synthesized with the same above method, and PCR was performed using cloning_F(1042-1061) which is designed in human VEGFR2 intron13 and cloning_R2.

Western Blot

After nucleofection, cells were cultured in a 75 cm² flask for three days without changing the medium. After three days the media was collected and cell debris was removed by centrifugation. Trichloroacetic acid (20% (w/v), Fisher Scientific, Pittsburgh, Pa.) was added to concentrate the supernatant (final concentration of trichloroacetic acid was 10%). Cells were incubated in trichloroacetic acid for 30 minutes on ice and then centrifuged at ×12000 g 4° C. for 5 minutes. Supernatants were discarded and cold acetone was added to the pellet. Centrifugation was repeated, the acetone was discarded and 800 μl of RIPA buffer (Sigma Aldrich, St. Louis, Mo.) was added. Samples were sonicated and proteins were separated by SDS-PAGE under reducing conditions. The same primary antibody as in flow cytometry was used at a 1:1000 dilution.

Intravitreous Injection

To examine whether moVEGFR2_MOe13 could work in the mouse eye, on day 0 and day 3 2 μl of 100 ng/μl moVEGFR2_MOe13 or STD_MO or DPBS were injected intravitreously. On day 4, retinal total RNA was extracted with RNeasy mini kit with DNaseI treatment. sVEGFR2 and mbVEGFR2 mRNA expression were determined by the method described above. For western blot of mbVEGFR2, on day 4, retina was dissolved in RIPA buffer. For western blot of sVEGFR2, on 4 day, intraocular solution was obtained from 6 eyes by pipette. After centrifuge, supernatant was used for further experiment. For western blot, biotin-conjugated anti-VEGFR2 (BAF644, R&D Systems, Minneapolis, Minn.) was used at 1 μg/μl.

Mouse Corneal Injury and Observation of CD31 and LYVE-1 in Cornea Flatmount

Figure 13C:
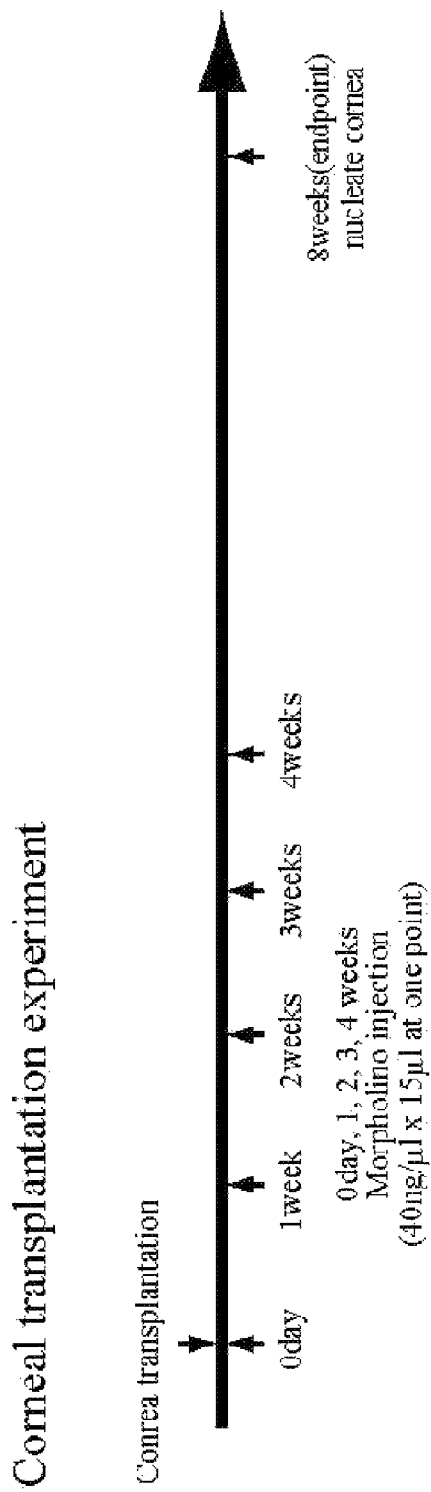
FIG. 13 shows laser photocoagulation, intravitreous injection, and CNV measurement conditions described in accordance with another embodiment of the present invention.

Experimental conditions were listed in FIG. 13. Under anesthesia, 15 μl of moVEGFR2_MOe13 (40 ng/μl), STD_MO (40 ng/μl) or DPBS was injected subconjunctivally into two different places one day prior to the placement of 2 symmetrical 11-0 nylon sutures, followed by re-injection at four days after suture placement. Eyes were harvested 7 days after suture placement. In a second group, 15 μl of moVEGFR2_MOe13 (40 ng/μl), STD_MO (40 ng/μl) or DPBS was injected subconjunctivally into two different places one day prior to the placement of 2 symmetrical 11-0 nylon sutures. Subconjunctival injections were repeated at four, seven and ten days after suture placement. Eyes were harvested 14 days after suture placement. The corneas were fixed in acetone at room temperature for 20 minutes. After 4 washes in PBST (0.1% Tween20/PBS), the corneas were incubated in 3% BSA/PBS at 4° C. for 3 days. To detect CD31 and LYVE1, corneas were incubated in 3% BSA/PBS with FITC-conjugated rat anti-CD31 antibody (553372, 1:500, BD Biosciences, San Jose, Calif.) or rabbit anti-LYVE-1 (ab14917, 1:200, Abcam, Cambridge, Mass.) overnight at 4° C. After 3 washes in PBST, the corneas were incubated in 3% BSA/PBS with Alexa Fluor® 546 conjugated goat anti-rabbit IgG (A11071, 1:2000, Invitrogen Corporation, Carlsbad, Calif.) for one hour at room temperature. After 4 washes in PBST, corneas were mounted on slide glass with Fluoro-gel (Electron Microscopy Sciences, Hatfield. Pa.). Fluorescence was observed by fluorescence microscope (Carl Zeiss MicroImaging, Inc., Thornwood, N.Y.). The data for each suture was calculated by ImageJ separately. Areas where sutures had fallen out were not included in the final calculations.

Mouse Corneal Transplantation

Mouse corneal transplantation has been described previously. The donor cornea was marked with 2 mm trephine, the anterior chamber was penetrated using a knife (ClearCut™, Alcon, Inc) and the cornea was cut with Vannas scissors and then placed in Balanced Salt Solution (BSS® Alcon Laboratories, Inc, Fort Worth). The recipient mouse was anesthetized by intramuscular injection with ketamine (100 mg/kg body weight) and xylazine (20 mg/kg body weight). To dilate pupil and anesthetize the cornea, 1% tropicamide ophthalmic solution and 0.5% proparacaine ophthalmic solution were used. The recipient's right cornea was marked with 1.5 mm trephine and removed by the same method as the donor cornea. Viscoelastic material (Healon®, 1% sodium hyaluronate, Abbott Medical Optics, IL) was used during recipient cornea dissection. The donor graft was sutured into the recipient bed using interrupted sutures (11-0 nylon, CS160-6, ETHICON, INC). After the transplantation, the eye was covered with 0.5% erythromycin ophthalmic ointment and the lid was sutured with 8-0 coated vicryl (BV130-5, ETHICON, INC). All sutures remained for the postoperative 1 week. We injected 15 μl moVEGFR2_MOe13 (40 ng/μl), STD_MO (40 ng/μl) or DPBS subconjunctivally on the day of transplantation, and postoperative 1, 2, 3, and 4 weeks (FIG. 13). The corneal opacity was examined weekly using operating microscope by the endpoint (8 weeks). The opacity was graded (from 0 to 5) to determine graft rejection. Opacity of grade 3 or more was considered to be graft rejection. At the 8 weeks, the corneas were harvested and subjected for CD31 and LYVE1 stain using the method described above.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

The invention claimed is:

1. A pharmaceutical composition for increasing expression of sVEGFR2 in a subject comprising a pharmaceutically effective carrier including a morpholino capable of binding to an exon13-intron13 splicing site of VEGFR2 mRNA to facilitate increased expression of sVEGFR2, wherein the morpholino is selected from SEQ ID NOs: 1, 2, 3, 20, 21, 22, 23, 24, 25, 26, 27, 28, 29, 30, 31, 32, 33, 34, 35, 36, 37, 38, 39, 40, 41, 42, or 43.

2. The composition of claim 1, wherein the morpholino has a sequence of SEQ ID NO: 001.

3. A method of increasing expression of sVEGFR2 in a subject, comprising administering to the subject an antisense morpholino capable of binding to an exon13-intron13 splicing site of VEGFR2 mRNA such that the VEGFR2 mRNA is spliced into a sVEGFR2 isoform, wherein the morpholino is selected from SEQ ID NOs: 1, 2, 3, 20, 21, 22, 23, 24, 25, 26, 27, 28, 29, 30, 31, 32, 33, 34, 35, 36, 37, 38, 39, 40, 41, 42, or 43.

4. The method of claim 3, wherein the morpholino has a sequence of SEQ ID NO: 001.

5. A method of inhibiting neovascularization in a subject, comprising administering to the subject an antisense morpholino capable of binding to an exon13-intron13 splicing site of VEGFR2 mRNA such that the VEGFR2 mRNA is spliced into a sVEGFR2 isoform, wherein the morpholino is selected from SEQ ID NOs: 1, 2, 3, 20, 21, 22, 23, 24, 25, 26, 27, 28, 29, 30, 31, 32, 33, 34, 35, 36, 37, 38, 39, 40, 41, 42, or 43.

6. The method of claim 5, wherein the morpholino has a sequence of SEQ ID NO: 001.

* * * * *